US008409830B2

(12) United States Patent
Hoff et al.

(10) Patent No.: US 8,409,830 B2
(45) Date of Patent: Apr. 2, 2013

(54) POLYPEPTIDES HAVING ISOAMYLASE ACTIVITY AND METHODS OF USE

(75) Inventors: Tine Hoff, Holte (DK); Carsten Sjoeholm, Alleroed (DK); Barrie Edmund Norman, Birkeroed (DK)

(73) Assignee: Novozymes A/S, Bagsvaerd (DK)

( * ) Notice: Subject to any disclaimer, the term of this patent is extended or adjusted under 35 U.S.C. 154(b) by 231 days.

(21) Appl. No.: 12/859,993

(22) Filed: Aug. 20, 2010

(65) Prior Publication Data

US 2011/0045136 A1   Feb. 24, 2011

Related U.S. Application Data

(60) Provisional application No. 61/237,805, filed on Aug. 28, 2009.

(30) Foreign Application Priority Data

Aug. 21, 2009   (EP) .................................... 09168390

(51) Int. Cl.
| C12P 19/16 | (2006.01) |
| C12P 19/22 | (2006.01) |
| C12P 19/20 | (2006.01) |
| C12P 19/14 | (2006.01) |
| C12N 9/44  | (2006.01) |

(52) U.S. Cl. ................ 435/98; 435/95; 435/96; 435/99; 435/210

(58) Field of Classification Search .................. None
See application file for complete search history.

(56) References Cited

U.S. PATENT DOCUMENTS

| 4,335,208 | A | | 6/1982 | Norman |
| 6,129,788 | A | * | 10/2000 | Liaw et al. ....................... 127/40 |
| 6,265,197 | B1 | * | 7/2001 | Bisg.ang.rd-Frantzen et al. ............................ 435/210 |

FOREIGN PATENT DOCUMENTS

| EP | 0 302 838 B1 | 6/1994 |
| EP | 0 327 391 B1 | 8/1997 |
| EP | 1 002 062 B1 | 5/2006 |
| WO | 99/28448 A1 | 6/1999 |
| WO | WO 2005/121305 A1 | 12/2005 |
| WO | 2009/009142 A2 | 1/2009 |

OTHER PUBLICATIONS

Abad et al., Geneseq Accession No. AVA64905 (2009).
Abad et al., Geneseq Accession No. AVA77075 (2009).
Amemura et al., Journal of Biological Chemistry, vol. 263, No. 19, pp. 9271-9275 (1988).
Amemura et al., UniProt Accession No. P10342 (1988).
Norman, Enzymes and Food Processing, chapter 2—New Developments in Starch Syrup Technology, pp. 38-50 (1980).
Tognoni et al., Journal of General Microbiology, vol. 135, pp. 37-45 (1989).
Xie et al., International Journal of Systematic and Evolutionary Microbiology, vol. 55, No. 2, pp. 753-756 (2005).
Thompson et al., GenBank Accession No. AAA25855 (1999).

* cited by examiner

*Primary Examiner* — David J Steadman
(74) *Attorney, Agent, or Firm* — Elias Lambiris

(57) ABSTRACT

The present invention relates to isolated polypeptides having isoamylase activity derived from *Dyella japonica* and isolated polynucleotides encoding the polypeptides. The invention also relates to nucleic acid constructs, vectors, and host cells comprising the polynucleotides as well as methods of producing and using the polypeptides. The invention also relates to the use of said polypeptide having isoamylase activity for producing glucose syrup, fructose syrup, maltose syrup or maltitol.

15 Claims, No Drawings

SEQUENCE LISTING

```
<160> NUMBER OF SEQ ID NOS: 25

<210> SEQ ID NO 1
<211> LENGTH: 2328
<212> TYPE: DNA
<213> ORGANISM: Dyella japonica
<220> FEATURE:
<221> NAME/KEY: CDS
<222> LOCATION: (1)..(2328)
<220> FEATURE:
<221> NAME/KEY: misc_signal
<222> LOCATION: (1)..(78)
<220> FEATURE:
<221> NAME/KEY: mat_peptide
<222> LOCATION: (79)..(2328)

<400> SEQUENCE: 1 atg aag tgc tca aca att ctc gcc gcg ctg ctg ggc tgc gcg gtg ctt       48
Met Lys Cys Ser Thr Ile Leu Ala Ala Leu Leu Gly Cys Ala Val Leu
    -25                 -20                 -15
```

| | | |
|---|---|---|
| gcc agt gtg ccc gca aca ccg gct cac gca acc atc aac agc atg acc<br>Ala Ser Val Pro Ala Thr Pro Ala His Ala Thr Ile Asn Ser Met Thr<br>-10                -5                    -1  1                   5 | 96 |
| ttg ggt gcg agc tat aac gcg caa aag acc agc atc acc ttc cgc gtg<br>Leu Gly Ala Ser Tyr Asn Ala Gln Lys Thr Ser Ile Thr Phe Arg Val<br>          10                   15                   20 | 144 |
| tat tcg tcc act gcc acg cgc atc gtg ttg tat ctc tat tcg gcc ggc<br>Tyr Ser Ser Thr Ala Thr Arg Ile Val Leu Tyr Leu Tyr Ser Ala Gly<br>     25                   30                   35 | 192 |
| tac ggc gcg cag gag tcg gcg acc tat acg ttg agt tcg gtc ggc agc<br>Tyr Gly Ala Gln Glu Ser Ala Thr Tyr Thr Leu Ser Ser Val Gly Ser<br> 40                   45                   50 | 240 |
| ggc gtc tgg gcg gtg acg gtg ccg gtg tcg tcg atc cag gcg gcc ggc<br>Gly Val Trp Ala Val Thr Val Pro Val Ser Ser Ile Gln Ala Ala Gly<br>55                60                   65                   70 | 288 |
| atc acc ggc gcg gtg tat tac ggc tat cgc gcc tgg ggc ccg aac tgg<br>Ile Thr Gly Ala Val Tyr Tyr Gly Tyr Arg Ala Trp Gly Pro Asn Trp<br>                   75                   80                   85 | 336 |
| ccg tat agc gcc agc tgg ggc aag ggc tcg cag gcg ggt ttt gtg tcc<br>Pro Tyr Ser Ala Ser Trp Gly Lys Gly Ser Gln Ala Gly Phe Val Ser<br>     90                   95                   100 | 384 |
| gac gtg gac agc agc ggc aac cgc ttc aat ccc aac aag ctg ctg ctc<br>Asp Val Asp Ser Ser Gly Asn Arg Phe Asn Pro Asn Lys Leu Leu Leu<br>         105                  110                 115 | 432 |
| gat ccg tat gcg cag gaa gtg agc cag gac ccg cag aat ccg tcg aac<br>Asp Pro Tyr Ala Gln Glu Val Ser Gln Asp Pro Gln Asn Pro Ser Asn<br>120                   125                  130 | 480 |
| cag aac ggc aac gtg ttc gcc tcc ggc gcc agt tat cgc act acc gac<br>Gln Asn Gly Asn Val Phe Ala Ser Gly Ala Ser Tyr Arg Thr Thr Asp<br>135                   140                 145                150 | 528 |
| agc ggc atc tat gca ccc aag ggc gtg gtg ctg gcc ccc agc acg cag<br>Ser Gly Ile Tyr Ala Pro Lys Gly Val Val Leu Ala Pro Ser Thr Gln<br>                   155                 160                165 | 576 |
| agc acg ggc agc aag ccg acg cgg gca cag aaa gac gat gtg atc tac<br>Ser Thr Gly Ser Lys Pro Thr Arg Ala Gln Lys Asp Asp Val Ile Tyr<br>         170                  175                 180 | 624 |
| gaa gtg cat gtg cgc ggt ttt acc gag cag gac agc tcg att cct gcg<br>Glu Val His Val Arg Gly Phe Thr Glu Gln Asp Ser Ser Ile Pro Ala<br>             185                  190                 195 | 672 |
| caa tat cgc ggc act tat tac ggc gcc gga ttg aag gcg agc tat ctg<br>Gln Tyr Arg Gly Thr Tyr Tyr Gly Ala Gly Leu Lys Ala Ser Tyr Leu<br>     200                   205                 210 | 720 |
| gcc agc ctc ggc gtc acg gcg gtg gaa ttc ctg ccc gtg cag gaa acc<br>Ala Ser Leu Gly Val Thr Ala Val Glu Phe Leu Pro Val Gln Glu Thr<br>215                   220                 225                230 | 768 |
| cag aac gac gcc aac gat gtg gtg ccc aac tcg gat gcc aac cag aat<br>Gln Asn Asp Ala Asn Asp Val Val Pro Asn Ser Asp Ala Asn Gln Asn<br>                   235                 240                245 | 816 |
| tac tgg ggc tat atg acc gag aat tat ttt tcg ccc gat cgc cgc tac<br>Tyr Trp Gly Tyr Met Thr Glu Asn Tyr Phe Ser Pro Asp Arg Arg Tyr<br>         250                  255                 260 | 864 |
| gcc tat aac aag gcc gcg ggc ggc ccc acg gct gaa ttc cag gcg atg<br>Ala Tyr Asn Lys Ala Ala Gly Gly Pro Thr Ala Glu Phe Gln Ala Met<br>             265                  270                 275 | 912 |
| gtg cag gcg ttc cac aac gca ggc atc aag gtc tat atg gac gtg gtc<br>Val Gln Ala Phe His Asn Ala Gly Ile Lys Val Tyr Met Asp Val Val<br>280                   285                  290 | 960 |
| tac aac cac act gcc gag ggc ggt acc tgg acc ggc aac gat ccc acc<br>Tyr Asn His Thr Ala Glu Gly Gly Thr Trp Thr Gly Asn Asp Pro Thr<br>295                   300                 305                310 | 1008 |

```
acg gcg acc att tat tca tgg cgc ggc ctg gac aac ggc acg tac tac      1056
Thr Ala Thr Ile Tyr Ser Trp Arg Gly Leu Asp Asn Gly Thr Tyr Tyr
                315                 320                 325 gaa ctc acc gcc gat cat caa tat ttc tac gac aac acc ggt acg ggc      1104
Glu Leu Thr Ala Asp His Gln Tyr Phe Tyr Asp Asn Thr Gly Thr Gly
                330                 335                 340 gcg aac ttc aat acg tac aac acg gtg gcg cag aac ctg atc gtc gat      1152
Ala Asn Phe Asn Thr Tyr Asn Thr Val Ala Gln Asn Leu Ile Val Asp
                345                 350                 355 tcg ctg gcc tat tgg tcc aac acc atg ggc gtg gac ggc ttc cgc ttc      1200
Ser Leu Ala Tyr Trp Ser Asn Thr Met Gly Val Asp Gly Phe Arg Phe
        360                 365                 370 gat ctc gca tcg gtg ctg ggc aat agc tgc ctc aat gcg gcc tat acg      1248
Asp Leu Ala Ser Val Leu Gly Asn Ser Cys Leu Asn Ala Ala Tyr Thr
375                 380                 385                 390 tcg gcg gcg ccc aat tgc ccc aac ggc ggc tac aac ttc gat gcg gcc      1296
Ser Ala Ala Pro Asn Cys Pro Asn Gly Gly Tyr Asn Phe Asp Ala Ala
                395                 400                 405 gac agc aat gtg gcg atc aac cgc atc ctg cgc gag ttc acc gtg cgt      1344
Asp Ser Asn Val Ala Ile Asn Arg Ile Leu Arg Glu Phe Thr Val Arg
                410                 415                 420 ccc gcg gca ggc ggc agc ggt ctg gat ctg ttt gcc gaa ccg tgg gcg      1392
Pro Ala Ala Gly Gly Ser Gly Leu Asp Leu Phe Ala Glu Pro Trp Ala
            425                 430                 435 atc ggt ggc aat tcg tat caa ttg ggc ggc ttt ccc aag ggc tgg tcg      1440
Ile Gly Gly Asn Ser Tyr Gln Leu Gly Gly Phe Pro Lys Gly Trp Ser
440                 445                 450 gaa tgg aac ggc ttg ttc cgc gac agc ctg cgc cag gcg cag aac cag      1488
Glu Trp Asn Gly Leu Phe Arg Asp Ser Leu Arg Gln Ala Gln Asn Gln
455                 460                 465                 470 ctg ggc agc acg acg atc tac atc acc cag gac gcc aac gat ttc tcc      1536
Leu Gly Ser Thr Thr Ile Tyr Ile Thr Gln Asp Ala Asn Asp Phe Ser
                475                 480                 485 ggt tcg tcc aat ctg ttc cag gcc agc ggg cgc gcg ccg tgg aac tcg      1584
Gly Ser Ser Asn Leu Phe Gln Ala Ser Gly Arg Ala Pro Trp Asn Ser
                490                 495                 500 gtc aac ttc atc gat gtg cac gac ggc ctg acc ttg aag gac gtc tat      1632
Val Asn Phe Ile Asp Val His Asp Gly Leu Thr Leu Lys Asp Val Tyr
                505                 510                 515 tcg tgc aat ggc gcc aac aac agc cag gcc tgg ccg tac gga ccc tcc      1680
Ser Cys Asn Gly Ala Asn Asn Ser Gln Ala Trp Pro Tyr Gly Pro Ser
        520                 525                 530 gac ggt ggc acc agc acc aac tac agc tgg gat cag ggc atg tcg gcg      1728
Asp Gly Gly Thr Ser Thr Asn Tyr Ser Trp Asp Gln Gly Met Ser Ala
535                 540                 545                 550 ggc acg ggc acc gca ttg gat cag cgt cgt gcc gca cgc acc ggc atg      1776
Gly Thr Gly Thr Ala Leu Asp Gln Arg Arg Ala Ala Arg Thr Gly Met
                555                 560                 565 gcc ttt gag atg ctc tcg gcc ggt acg ccg ctg atg cag ggc ggc gac      1824
Ala Phe Glu Met Leu Ser Ala Gly Thr Pro Leu Met Gln Gly Gly Asp
            570                 575                 580 gaa cac ctg cgc aca ctc cag tgc aac aac aat gcg tac aac ctc gac      1872
Glu His Leu Arg Thr Leu Gln Cys Asn Asn Asn Ala Tyr Asn Leu Asp
                585                 590                 595 tcc agc gcg aac tgg ctg agc agc agc tgg acc gcc gat cag acc aac      1920
Ser Ser Ala Asn Trp Leu Ser Ser Ser Trp Thr Ala Asp Gln Thr Asn
            600                 605                 610 ttc tac acc ttc gcc cag cgt ctg atc gcc ttc cgc aaa gcc cat ccg      1968
Phe Tyr Thr Phe Ala Gln Arg Leu Ile Ala Phe Arg Lys Ala His Pro
615                 620                 625                 630
```

```
gca ctg cgt ccg gcc agc tgg tac agc ggc agc cag ctg gtc tgg tat    2016
Ala Leu Arg Pro Ala Ser Trp Tyr Ser Gly Ser Gln Leu Val Trp Tyr
            635                 640                 645 caa ccc agc ggt gcg gtg gcg gat acc aac tac tgg aac aac acc agt    2064
Gln Pro Ser Gly Ala Val Ala Asp Thr Asn Tyr Trp Asn Asn Thr Ser
        650                 655                 660 aac tac gca ctg gct tac acc atc aac ggg tcg tcg ctg ggc gac ggc    2112
Asn Tyr Ala Leu Ala Tyr Thr Ile Asn Gly Ser Ser Leu Gly Asp Gly
    665                 670                 675 aat tct atc tat gtc gcc tac aac ggc tgg tcc ggc agc gtc acc ttc    2160
Asn Ser Ile Tyr Val Ala Tyr Asn Gly Trp Ser Gly Ser Val Thr Phe
680                 685                 690 acc ttg cct gcg ccg ccc acg ggc acg cag tgg tac cgc gtc acg gat    2208
Thr Leu Pro Ala Pro Pro Thr Gly Thr Gln Trp Tyr Arg Val Thr Asp
695                 700                 705                 710 acc tgc aac tgg aac gac ggc gcc aat act ttc gtg gcg ccc ggc agt    2256
Thr Cys Asn Trp Asn Asp Gly Ala Asn Thr Phe Val Ala Pro Gly Ser
                715                 720                 725 gag acg ctg atc ggc gga gca ggg acg act tat ggc cag tgc ggt cag    2304
Glu Thr Leu Ile Gly Gly Ala Gly Thr Thr Tyr Gly Gln Cys Gly Gln
            730                 735                 740 tcg ctg ttg ttg ttg att tcg aag                                    2328
Ser Leu Leu Leu Leu Ile Ser Lys
            745                 750

<210> SEQ ID NO 2
<211> LENGTH: 776
<212> TYPE: PRT
<213> ORGANISM: Dyella japonica

<400> SEQUENCE: 2

Met Lys Cys Ser Thr Ile Leu Ala Ala Leu Leu Gly Cys Ala Val Leu
    -25                 -20                 -15

Ala Ser Val Pro Ala Thr Pro Ala His Ala Thr Ile Asn Ser Met Thr
-10                  -5                 -1   1               5

Leu Gly Ala Ser Tyr Asn Ala Gln Lys Thr Ser Ile Thr Phe Arg Val
                10                  15                  20

Tyr Ser Ser Thr Ala Thr Arg Ile Val Leu Tyr Leu Tyr Ser Ala Gly
            25                  30                  35

Tyr Gly Ala Gln Glu Ser Ala Thr Tyr Thr Leu Ser Ser Val Gly Ser
        40                  45                  50

Gly Val Trp Ala Val Thr Val Pro Val Ser Ser Ile Gln Ala Ala Gly
55                  60                  65                  70

Ile Thr Gly Ala Val Tyr Tyr Gly Tyr Arg Ala Trp Gly Pro Asn Trp
                75                  80                  85

Pro Tyr Ser Ala Ser Trp Gly Lys Gly Ser Gln Ala Gly Phe Val Ser
            90                  95                  100

Asp Val Asp Ser Ser Gly Asn Arg Phe Asn Pro Asn Lys Leu Leu Leu
        105                 110                 115

Asp Pro Tyr Ala Gln Glu Val Ser Gln Asp Pro Gln Asn Pro Ser Asn
    120                 125                 130

Gln Asn Gly Asn Val Phe Ala Ser Gly Ala Ser Tyr Arg Thr Thr Asp
135                 140                 145                 150

Ser Gly Ile Tyr Ala Pro Lys Gly Val Val Leu Ala Pro Ser Thr Gln
                155                 160                 165

Ser Thr Gly Ser Lys Pro Thr Arg Ala Gln Lys Asp Asp Val Ile Tyr
            170                 175                 180
```

```
Glu Val His Val Arg Gly Phe Thr Glu Gln Asp Ser Ser Ile Pro Ala
            185                 190                 195

Gln Tyr Arg Gly Thr Tyr Tyr Gly Ala Gly Leu Lys Ala Ser Tyr Leu
            200                 205                 210

Ala Ser Leu Gly Val Thr Ala Val Glu Phe Leu Pro Val Gln Glu Thr
215                 220                 225                 230

Gln Asn Asp Ala Asn Asp Val Val Pro Asn Ser Asp Ala Asn Gln Asn
            235                 240                 245

Tyr Trp Gly Tyr Met Thr Glu Asn Tyr Phe Ser Pro Asp Arg Arg Tyr
            250                 255                 260

Ala Tyr Asn Lys Ala Ala Gly Gly Pro Thr Ala Glu Phe Gln Ala Met
            265                 270                 275

Val Gln Ala Phe His Asn Ala Gly Ile Lys Val Tyr Met Asp Val Val
280                 285                 290

Tyr Asn His Thr Ala Glu Gly Gly Thr Trp Thr Gly Asn Asp Pro Thr
295                 300                 305                 310

Thr Ala Thr Ile Tyr Ser Trp Arg Gly Leu Asp Asn Gly Thr Tyr Tyr
            315                 320                 325

Glu Leu Thr Ala Asp His Gln Tyr Phe Tyr Asp Asn Thr Gly Thr Gly
            330                 335                 340

Ala Asn Phe Asn Thr Tyr Asn Thr Val Ala Gln Asn Leu Ile Val Asp
            345                 350                 355

Ser Leu Ala Tyr Trp Ser Asn Thr Met Gly Val Asp Gly Phe Arg Phe
360                 365                 370

Asp Leu Ala Ser Val Leu Gly Asn Ser Cys Leu Asn Ala Ala Tyr Thr
375                 380                 385                 390

Ser Ala Ala Pro Asn Cys Pro Asn Gly Gly Tyr Asn Phe Asp Ala Ala
            395                 400                 405

Asp Ser Asn Val Ala Ile Asn Arg Ile Leu Arg Glu Phe Thr Val Arg
            410                 415                 420

Pro Ala Ala Gly Gly Ser Gly Leu Asp Leu Phe Ala Glu Pro Trp Ala
            425                 430                 435

Ile Gly Gly Asn Ser Tyr Gln Leu Gly Gly Phe Pro Lys Gly Trp Ser
            440                 445                 450

Glu Trp Asn Gly Leu Phe Arg Asp Ser Leu Arg Gln Ala Gln Asn Gln
455                 460                 465                 470

Leu Gly Ser Thr Thr Ile Tyr Ile Thr Gln Asp Ala Asn Asp Phe Ser
                475                 480                 485

Gly Ser Ser Asn Leu Phe Gln Ala Ser Gly Arg Ala Pro Trp Asn Ser
            490                 495                 500

Val Asn Phe Ile Asp Val His Asp Gly Leu Thr Leu Lys Asp Val Tyr
            505                 510                 515

Ser Cys Asn Gly Ala Asn Asn Ser Gln Ala Trp Pro Tyr Gly Pro Ser
            520                 525                 530

Asp Gly Gly Thr Ser Thr Asn Tyr Ser Trp Asp Gln Gly Met Ser Ala
535                 540                 545                 550

Gly Thr Gly Thr Ala Leu Asp Gln Arg Arg Ala Ala Arg Thr Gly Met
                555                 560                 565

Ala Phe Glu Met Leu Ser Ala Gly Thr Pro Leu Met Gln Gly Gly Asp
            570                 575                 580

Glu His Leu Arg Thr Leu Gln Cys Asn Asn Asn Ala Tyr Asn Leu Asp
            585                 590                 595

Ser Ser Ala Asn Trp Leu Ser Ser Trp Thr Ala Asp Gln Thr Asn
600                 605                 610
```

-continued

```
Phe Tyr Thr Phe Ala Gln Arg Leu Ile Ala Phe Arg Lys Ala His Pro
615                 620                 625                 630

Ala Leu Arg Pro Ala Ser Trp Tyr Ser Gly Ser Gln Leu Val Trp Tyr
                635                 640                 645

Gln Pro Ser Gly Ala Val Ala Asp Thr Asn Tyr Trp Asn Asn Thr Ser
            650                 655                 660

Asn Tyr Ala Leu Ala Tyr Thr Ile Asn Gly Ser Ser Leu Gly Asp Gly
        665                 670                 675

Asn Ser Ile Tyr Val Ala Tyr Asn Gly Trp Ser Gly Ser Val Thr Phe
    680                 685                 690

Thr Leu Pro Ala Pro Pro Thr Gly Thr Gln Trp Tyr Arg Val Thr Asp
695                 700                 705                 710

Thr Cys Asn Trp Asn Asp Gly Ala Asn Thr Phe Val Ala Pro Gly Ser
                715                 720                 725

Glu Thr Leu Ile Gly Gly Ala Gly Thr Thr Tyr Gly Gln Cys Gly Gln
            730                 735                 740

Ser Leu Leu Leu Leu Ile Ser Lys
        745                 750

<210> SEQ ID NO 3
<211> LENGTH: 2331
<212> TYPE: DNA
<213> ORGANISM: Dyella japonica
<220> FEATURE:
<221> NAME/KEY: CDS
<222> LOCATION: (1)..(2328)
<220> FEATURE:
<221> NAME/KEY: sig_peptide
<222> LOCATION: (1)..(78)
<220> FEATURE:
<221> NAME/KEY: mat_peptide
<222> LOCATION: (79)..(2328)

<400> SEQUENCE: 3 atg aag tgc tcg aag att ctc gcc gcg ctg ctg gcc tgc gcg gtg ctc      48
Met Lys Cys Ser Lys Ile Leu Ala Ala Leu Leu Ala Cys Ala Val Leu
-25                 -20                 -15 acc ggc gtg ccc gca aca ccg gcc cag gcg gcc atc aac agc atg agt      96
Thr Gly Val Pro Ala Thr Pro Ala Gln Ala Ala Ile Asn Ser Met Ser
-10             -5                  -1  1               5 ctt ggc gcg agc tac aac gcg cag aag acc agc atc acc ttt cgc gtt     144
Leu Gly Ala Ser Tyr Asn Ala Gln Lys Thr Ser Ile Thr Phe Arg Val
            10                  15                  20 tac tcc tcc acc gcc acg cgc gtg gtg ctc tac ctg tat tcg gcc ggc     192
Tyr Ser Ser Thr Ala Thr Arg Val Val Leu Tyr Leu Tyr Ser Ala Gly
        25                  30                  35 tac ggc gtg cag gaa tcg acc acg tat gcg ctc agt tcg gtg ggt agc     240
Tyr Gly Val Gln Glu Ser Thr Thr Tyr Ala Leu Ser Ser Val Gly Ser
    40                  45                  50 ggc gta tgg gcg gtg acg gtg ccg gtg tcg tcg atc cag gcc gcg ggc     288
Gly Val Trp Ala Val Thr Val Pro Val Ser Ser Ile Gln Ala Ala Gly
55                  60                  65                  70 atc acc ggc tcg gtg tac tac ggc tat cgc gcg tgg ggt ccc aac tgg     336
Ile Thr Gly Ser Val Tyr Tyr Gly Tyr Arg Ala Trp Gly Pro Asn Trp
                75                  80                  85 ccg tac aac agc agc tgg ggc aag ggt tcg cag gcg ggc ttt gtt gct     384
Pro Tyr Asn Ser Ser Trp Gly Lys Gly Ser Gln Ala Gly Phe Val Ala
            90                  95                  100 gac gtc gac gcc agc ggc aac cga ttc aat ccc aac aag ctg ctg ctc     432
Asp Val Asp Ala Ser Gly Asn Arg Phe Asn Pro Asn Lys Leu Leu Leu
        105                 110                 115
```

-continued

| | | |
|---|---|---|
| gat ccg tat gcg cag gaa gtg agc cag gat ccg cag aac ccg tcg aac<br>Asp Pro Tyr Ala Gln Glu Val Ser Gln Asp Pro Gln Asn Pro Ser Asn<br>120                             125                          130 | 480 |
| cag aac ggc aac gtg ttt gcc tcc ggc gcc agc tat cgc acc acc gac<br>Gln Asn Gly Asn Val Phe Ala Ser Gly Ala Ser Tyr Arg Thr Thr Asp<br>135                         140                       145                   150 | 528 |
| agc ggc atc tac gca ccc aag ggc gtg gtg ctg gcg ccc agc acg cag<br>Ser Gly Ile Tyr Ala Pro Lys Gly Val Val Leu Ala Pro Ser Thr Gln<br>                    155                       160                      165 | 576 |
| ggc acc ggc acc aag ccc acg cgt gcg cag aag gac gat gtg atc tac<br>Gly Thr Gly Thr Lys Pro Thr Arg Ala Gln Lys Asp Asp Val Ile Tyr<br>                  170                      175                     180 | 624 |
| gaa gtg cac gta cgc ggc ttc acc gaa cag gac agc tcc att ccc gcg<br>Glu Val His Val Arg Gly Phe Thr Glu Gln Asp Ser Ser Ile Pro Ala<br>185                         190                       195 | 672 |
| caa tat cgc ggc acg tat tac ggc gcg gga ttg aag gcg agc tat ctc<br>Gln Tyr Arg Gly Thr Tyr Tyr Gly Ala Gly Leu Lys Ala Ser Tyr Leu<br>        200                    205                    210 | 720 |
| gcc agc ctc ggc gtc acc gcg gtg gaa ttc ctg ccc gtg cag gaa acg<br>Ala Ser Leu Gly Val Thr Ala Val Glu Phe Leu Pro Val Gln Glu Thr<br>215                       220                     225                   230 | 768 |
| cag aat gac gcc aac gac gtg gtg ccc aac tcg gat gcc aac cag aac<br>Gln Asn Asp Ala Asn Asp Val Val Pro Asn Ser Asp Ala Asn Gln Asn<br>                  235                      240                   245 | 816 |
| tac tgg ggc tac atg acc gag aac tat ttt tcg ccc gat cga cgc tat<br>Tyr Trp Gly Tyr Met Thr Glu Asn Tyr Phe Ser Pro Asp Arg Arg Tyr<br>                250                    255                    260 | 864 |
| gcg tac aac aag gcg ccc ggc ggt ccc acg gcg gaa ttc cag gcg atg<br>Ala Tyr Asn Lys Ala Pro Gly Gly Pro Thr Ala Glu Phe Gln Ala Met<br>265                       270                     275 | 912 |
| gtg cag gcg ttc cac aac gcc ggc atc aag gtc tac atg gac gtg gtc<br>Val Gln Ala Phe His Asn Ala Gly Ile Lys Val Tyr Met Asp Val Val<br>        280                    285                    290 | 960 |
| tac aac cac acc gcc gaa ggc ggc acc tgg acg ggc agc gat ccc acc<br>Tyr Asn His Thr Ala Glu Gly Gly Thr Trp Thr Gly Ser Asp Pro Thr<br>295                       300                    305                   310 | 1008 |
| acg gcc acc atc tat tcg tgg cgc ggc ctg gac aac ggc acg tac tac<br>Thr Ala Thr Ile Tyr Ser Trp Arg Gly Leu Asp Asn Gly Thr Tyr Tyr<br>                315                    320                   325 | 1056 |
| gaa ttg acg tcc ggt aac caa tat ttc tac gac aac acc ggc acc ggc<br>Glu Leu Thr Ser Gly Asn Gln Tyr Phe Tyr Asp Asn Thr Gly Thr Gly<br>        330                    335                    340 | 1104 |
| gcg aac ttc aac acg tac aac acg gtg gcg cag aac ctg atc gtg gac<br>Ala Asn Phe Asn Thr Tyr Asn Thr Val Ala Gln Asn Leu Ile Val Asp<br>345                         350                      355 | 1152 |
| tcg ctc gcg tat tgg gcc aac acg atg ggc gtg gat ggt ttc cgt ttt<br>Ser Leu Ala Tyr Trp Ala Asn Thr Met Gly Val Asp Gly Phe Arg Phe<br>360                       365                    370 | 1200 |
| gat ctc gcc tcg gta ctg ggc aac agc tgc ctc aac ggt gcg tac acg<br>Asp Leu Ala Ser Val Leu Gly Asn Ser Cys Leu Asn Gly Ala Tyr Thr<br>375                       380                    385                   390 | 1248 |
| tcg tcg gcg ccg aac tgc ccc agc ggc ggc tac aac ttc gac gcg gcg<br>Ser Ser Ala Pro Asn Cys Pro Ser Gly Gly Tyr Asn Phe Asp Ala Ala<br>                395                    400                   405 | 1296 |
| gat tcg aac gtc gcc atc aac cgc atc ctg cgc gaa ttc acc gtg cgt<br>Asp Ser Asn Val Ala Ile Asn Arg Ile Leu Arg Glu Phe Thr Val Arg<br>        410                    415                    420 | 1344 |
| ccg tcc ggc ggc ggc agt ggc ctg gac ctg ttt gcg gag ccc tgg gcc<br>Pro Ser Gly Gly Gly Ser Gly Leu Asp Leu Phe Ala Glu Pro Trp Ala<br>425                       430                    435 | 1392 |

```
atc ggc ggc aat tcg tat cag ctt ggc ggt ttt ccg cag ggt tgg tcc    1440
Ile Gly Gly Asn Ser Tyr Gln Leu Gly Gly Phe Pro Gln Gly Trp Ser
440                 445                 450 gaa tgg aac ggc ctg ttc cgc gac agc ctg cgc cag gcg cag aac gaa    1488
Glu Trp Asn Gly Leu Phe Arg Asp Ser Leu Arg Gln Ala Gln Asn Glu
455                 460                 465                 470 ctg ggc agc atg acc atc cac att acg cag gat gcg aac gac ttc tcc    1536
Leu Gly Ser Met Thr Ile His Ile Thr Gln Asp Ala Asn Asp Phe Ser
        475                 480                 485 ggt tcg tcc aac ctg ttc cag gcc aat gga cgc tcg ccg tgg aac tcg    1584
Gly Ser Ser Asn Leu Phe Gln Ala Asn Gly Arg Ser Pro Trp Asn Ser
        490                 495                 500 gtg aac ttc atc gac gtg cat gac ggc atg acc ttg aag gac gtc tat    1632
Val Asn Phe Ile Asp Val His Asp Gly Met Thr Leu Lys Asp Val Tyr
        505                 510                 515 tcg tgc aac ggc gcc aac aac agc cag gcc tgg ccg tac ggg ccc tcc    1680
Ser Cys Asn Gly Ala Asn Asn Ser Gln Ala Trp Pro Tyr Gly Pro Ser
520                 525                 530 gat ggc ggc acc agc acc aac tac agc tgg gat cag ggc atg tcc gcg    1728
Asp Gly Gly Thr Ser Thr Asn Tyr Ser Trp Asp Gln Gly Met Ser Ala
535                 540                 545                 550 ggc acc ggc acg gcg ttg gat caa cgc cgc gcg gcc cgc acg ggc atg    1776
Gly Thr Gly Thr Ala Leu Asp Gln Arg Arg Ala Ala Arg Thr Gly Met
                555                 560                 565 gcg ttc gaa atg ctc tcg gca ggc acg ccg ctg atg cag ggc ggc gac    1824
Ala Phe Glu Met Leu Ser Ala Gly Thr Pro Leu Met Gln Gly Gly Asp
        570                 575                 580 gaa cac ctg cgc acg ctt cag tgc aac aac aac gcc tac aac ctc gat    1872
Glu His Leu Arg Thr Leu Gln Cys Asn Asn Asn Ala Tyr Asn Leu Asp
        585                 590                 595 tcc agc gcc aac tgg ctc agc agt agc tgg acc acc gac cag tcg aat    1920
Ser Ser Ala Asn Trp Leu Ser Ser Ser Trp Thr Thr Asp Gln Ser Asn
600                 605                 610 ttc tac act tac gcc cag cgc ctg atc gcc ttc cgc aag gcg cat ccc    1968
Phe Tyr Thr Tyr Ala Gln Arg Leu Ile Ala Phe Arg Lys Ala His Pro
615                 620                 625                 630 gcg ctg cgt ccc gcc agt tgg tac agc ggc agc caa ctg gtg tgg tac    2016
Ala Leu Arg Pro Ala Ser Trp Tyr Ser Gly Ser Gln Leu Val Trp Tyr
                635                 640                 645 caa ccc agc ggc gtg gca gcg gac agc agt tac tgg aac aac acc agc    2064
Gln Pro Ser Gly Val Ala Ala Asp Ser Ser Tyr Trp Asn Asn Thr Ser
        650                 655                 660 aac tac gcg att gcg tac acc atc aac ggc ccg tcg ctg ggc gac aga    2112
Asn Tyr Ala Ile Ala Tyr Thr Ile Asn Gly Pro Ser Leu Gly Asp Arg
        665                 670                 675 aac tcc atc tac gtc gcc tat aac ggc tgg tcg ggc agc gtc acc ttc    2160
Asn Ser Ile Tyr Val Ala Tyr Asn Gly Trp Ser Gly Ser Val Thr Phe
        680                 685                 690 acc ttg ccg gcg ccg cca tcg ggc acg cag tgg tat cgc gtc acc gat    2208
Thr Leu Pro Ala Pro Pro Ser Gly Thr Gln Trp Tyr Arg Val Thr Asp
695                 700                 705                 710 acg tgc aac tgg aac gac ggc gca aat act ttc gtt gcg ccc ggc agc    2256
Thr Cys Asn Trp Asn Asp Gly Ala Asn Thr Phe Val Ala Pro Gly Ser
                715                 720                 725 gaa acg ctg atc ggt ggg gca ggg acc acg tac ggc cag tgc ggc cag    2304
Glu Thr Leu Ile Gly Gly Ala Gly Thr Thr Tyr Gly Gln Cys Gly Gln
        730                 735                 740 tcg ttg ctg ctg ctg att tcc aaa taa                                2331
Ser Leu Leu Leu Leu Ile Ser Lys
        745                 750
```

<210> SEQ ID NO 4
<211> LENGTH: 776
<212> TYPE: PRT
<213> ORGANISM: Dyella japonica

<400> SEQUENCE: 4

```
Met Lys Cys Ser Lys Ile Leu Ala Ala Leu Leu Ala Cys Ala Val Leu
    -25             -20                 -15
Thr Gly Val Pro Ala Thr Pro Ala Gln Ala Ala Ile Asn Ser Met Ser
-10              -5              -1  1               5
Leu Gly Ala Ser Tyr Asn Ala Gln Lys Thr Ser Ile Thr Phe Arg Val
            10                  15                  20
Tyr Ser Ser Thr Ala Thr Arg Val Val Leu Tyr Leu Tyr Ser Ala Gly
        25                  30                  35
Tyr Gly Val Gln Glu Ser Thr Thr Tyr Ala Leu Ser Ser Val Gly Ser
    40                  45                  50
Gly Val Trp Ala Val Thr Val Pro Val Ser Ser Ile Gln Ala Ala Gly
55                  60                  65                  70
Ile Thr Gly Ser Val Tyr Tyr Gly Tyr Arg Ala Trp Gly Pro Asn Trp
                75                  80                  85
Pro Tyr Asn Ser Ser Trp Gly Lys Gly Ser Gln Ala Gly Phe Val Ala
            90                  95                  100
Asp Val Asp Ala Ser Gly Asn Arg Phe Asn Pro Asn Lys Leu Leu Leu
        105                 110                 115
Asp Pro Tyr Ala Gln Glu Val Ser Gln Asp Pro Gln Asn Pro Ser Asn
    120                 125                 130
Gln Asn Gly Asn Val Phe Ala Ser Gly Ala Ser Tyr Arg Thr Thr Asp
135                 140                 145                 150
Ser Gly Ile Tyr Ala Pro Lys Gly Val Val Leu Ala Pro Ser Thr Gln
                155                 160                 165
Gly Thr Gly Thr Lys Pro Thr Arg Ala Gln Lys Asp Asp Val Ile Tyr
            170                 175                 180
Glu Val His Val Arg Gly Phe Thr Glu Gln Asp Ser Ser Ile Pro Ala
        185                 190                 195
Gln Tyr Arg Gly Thr Tyr Tyr Gly Ala Gly Leu Lys Ala Ser Tyr Leu
    200                 205                 210
Ala Ser Leu Gly Val Thr Ala Val Glu Phe Leu Pro Val Gln Glu Thr
215                 220                 225                 230
Gln Asn Asp Ala Asn Asp Val Val Pro Asn Ser Asp Ala Asn Gln Asn
                235                 240                 245
Tyr Trp Gly Tyr Met Thr Glu Asn Tyr Phe Ser Pro Asp Arg Arg Tyr
            250                 255                 260
Ala Tyr Asn Lys Ala Pro Gly Gly Pro Thr Ala Glu Phe Gln Ala Met
        265                 270                 275
Val Gln Ala Phe His Asn Ala Gly Ile Lys Val Tyr Met Asp Val Val
    280                 285                 290
Tyr Asn His Thr Ala Glu Gly Gly Thr Trp Thr Gly Ser Asp Pro Thr
295                 300                 305                 310
Thr Ala Thr Ile Tyr Ser Trp Arg Gly Leu Asp Asn Gly Thr Tyr Tyr
                315                 320                 325
Glu Leu Thr Ser Gly Asn Gln Tyr Phe Tyr Asp Asn Thr Gly Thr Gly
            330                 335                 340
Ala Asn Phe Asn Thr Tyr Asn Thr Val Ala Gln Asn Leu Ile Val Asp
        345                 350                 355
```

```
Ser Leu Ala Tyr Trp Ala Asn Thr Met Gly Val Asp Gly Phe Arg Phe
    360                 365                 370

Asp Leu Ala Ser Val Leu Gly Asn Ser Cys Leu Asn Gly Ala Tyr Thr
375                 380                 385                 390

Ser Ser Ala Pro Asn Cys Pro Ser Gly Gly Tyr Asn Phe Asp Ala Ala
                395                 400                 405

Asp Ser Asn Val Ala Ile Asn Arg Ile Leu Arg Glu Phe Thr Val Arg
            410                 415                 420

Pro Ser Gly Gly Gly Ser Gly Leu Asp Leu Phe Ala Glu Pro Trp Ala
                425                 430                 435

Ile Gly Gly Asn Ser Tyr Gln Leu Gly Gly Phe Pro Gln Gly Trp Ser
    440                 445                 450

Glu Trp Asn Gly Leu Phe Arg Asp Ser Leu Arg Gln Ala Gln Asn Glu
455                 460                 465                 470

Leu Gly Ser Met Thr Ile His Ile Thr Gln Asp Ala Asn Asp Phe Ser
                475                 480                 485

Gly Ser Ser Asn Leu Phe Gln Ala Asn Gly Arg Ser Pro Trp Asn Ser
                490                 495                 500

Val Asn Phe Ile Asp Val His Asp Gly Met Thr Leu Lys Asp Val Tyr
            505                 510                 515

Ser Cys Asn Gly Ala Asn Asn Ser Gln Ala Trp Pro Tyr Gly Pro Ser
520                 525                 530

Asp Gly Gly Thr Ser Thr Asn Tyr Ser Trp Asp Gln Gly Met Ser Ala
535                 540                 545                 550

Gly Thr Gly Thr Ala Leu Asp Gln Arg Arg Ala Ala Arg Thr Gly Met
                555                 560                 565

Ala Phe Glu Met Leu Ser Ala Gly Thr Pro Leu Met Gln Gly Gly Asp
                570                 575                 580

Glu His Leu Arg Thr Leu Gln Cys Asn Asn Asn Ala Tyr Asn Leu Asp
                585                 590                 595

Ser Ser Ala Asn Trp Leu Ser Ser Trp Thr Thr Asp Gln Ser Asn
                600                 605                 610

Phe Tyr Thr Tyr Ala Gln Arg Leu Ile Ala Phe Arg Lys Ala His Pro
615                 620                 625                 630

Ala Leu Arg Pro Ala Ser Trp Tyr Ser Gly Ser Gln Leu Val Trp Tyr
                635                 640                 645

Gln Pro Ser Gly Val Ala Ala Asp Ser Ser Tyr Trp Asn Asn Thr Ser
                650                 655                 660

Asn Tyr Ala Ile Ala Tyr Thr Ile Asn Gly Pro Ser Leu Gly Asp Arg
            665                 670                 675

Asn Ser Ile Tyr Val Ala Tyr Asn Gly Trp Ser Gly Ser Val Thr Phe
            680                 685                 690

Thr Leu Pro Ala Pro Ser Gly Thr Gln Trp Tyr Arg Val Thr Asp
695                 700                 705                 710

Thr Cys Asn Trp Asn Asp Gly Ala Asn Thr Phe Val Ala Pro Gly Ser
                715                 720                 725

Glu Thr Leu Ile Gly Gly Ala Gly Thr Thr Tyr Gly Gln Cys Gly Gln
                730                 735                 740

Ser Leu Leu Leu Leu Ile Ser Lys
                745                 750

<210> SEQ ID NO 5
<211> LENGTH: 2328
<212> TYPE: DNA
```

-continued

```
<213> ORGANISM: Dyella japonica
<220> FEATURE:
<221> NAME/KEY: CDS
<222> LOCATION: (1)..(2328)
<220> FEATURE:
<221> NAME/KEY: sig_peptide
<222> LOCATION: (1)..(78)
<220> FEATURE:
<221> NAME/KEY: mat_peptide
<222> LOCATION: (79)..(2328)

<400> SEQUENCE: 5 atg aag tgc ccg aag atc ctc gcc gcg ctg ctg gcc tgc gcg gtg ctc      48
Met Lys Cys Pro Lys Ile Leu Ala Ala Leu Leu Ala Cys Ala Val Leu
    -25                 -20                 -15 gcc gcc gtg ccc gcc acg cca gtc cac gcg gcc atc aac agc atg agt      96
Ala Ala Val Pro Ala Thr Pro Val His Ala Ala Ile Asn Ser Met Ser
-10                  -5                  -1   1               5 ctt ggc gcg agc tac aac gcg gcg cag acc agc atc acc ttc cgc gtc     144
Leu Gly Ala Ser Tyr Asn Ala Ala Gln Thr Ser Ile Thr Phe Arg Val
                10                  15                  20 tat tcc tct acc gcc acg cga ctc gtg ctg tac gtg tat tcg gcc ggc     192
Tyr Ser Ser Thr Ala Thr Arg Leu Val Leu Tyr Val Tyr Ser Ala Gly
            25                  30                  35 tac ggc gtg cag gaa tcg gcc acc tat ccg ctc acc tcg gtg ggt agc     240
Tyr Gly Val Gln Glu Ser Ala Thr Tyr Pro Leu Thr Ser Val Gly Ser
    40                  45                  50 ggc gta tgg gcg gtg acg gtg ccg gtg tcg tcg atc cag gcg gca ggc     288
Gly Val Trp Ala Val Thr Val Pro Val Ser Ser Ile Gln Ala Ala Gly
55                  60                  65                  70 atc acc ggt tcg gtc tat tac ggc tat cgc gcc tgg gga ccg aac tgg     336
Ile Thr Gly Ser Val Tyr Tyr Gly Tyr Arg Ala Trp Gly Pro Asn Trp
                75                  80                  85 ccg tac aac agc agc tgg ggc aag ggt tcg cag gcc ggt ttt gta tcg     384
Pro Tyr Asn Ser Ser Trp Gly Lys Gly Ser Gln Ala Gly Phe Val Ser
            90                  95                  100 gac gtc gac gcc agc ggc aat cgt ttc aat ccg aac aag ctg ctg ctc     432
Asp Val Asp Ala Ser Gly Asn Arg Phe Asn Pro Asn Lys Leu Leu Leu
    105                 110                 115 gat ccg tat gcg cag gaa gtg agc cag gat ccg cag aac ccg tcg aac     480
Asp Pro Tyr Ala Gln Glu Val Ser Gln Asp Pro Gln Asn Pro Ser Asn
120                 125                 130 cag aac ggc aac gtg ttc gcc tcc ggc gcc agt tat cgc acc acc gac     528
Gln Asn Gly Asn Val Phe Ala Ser Gly Ala Ser Tyr Arg Thr Thr Asp
135                 140                 145                 150 agc ggc atc tat gcg ccc aag ggc gtg gtg ctc gcg ccc atc acg cag     576
Ser Gly Ile Tyr Ala Pro Lys Gly Val Val Leu Ala Pro Ile Thr Gln
                155                 160                 165 agc acc ggc agc aag ccc acg cgg gcg cag aag gac gac gtg atc tac     624
Ser Thr Gly Ser Lys Pro Thr Arg Ala Gln Lys Asp Asp Val Ile Tyr
            170                 175                 180 gaa gtc cac gtg cgc ggc ttc acc gag cag gac agc tcg atc gcg gcg     672
Glu Val His Val Arg Gly Phe Thr Glu Gln Asp Ser Ser Ile Ala Ala
    185                 190                 195 cag tat cgc ggc acc tac tac ggt gcc gga ctc aag gcg agt tat ctg     720
Gln Tyr Arg Gly Thr Tyr Tyr Gly Ala Gly Leu Lys Ala Ser Tyr Leu
200                 205                 210 gcc agc ctg ggc gtg acg gcg gtg gaa ttc ctg ccc gtg cag gaa acg     768
Ala Ser Leu Gly Val Thr Ala Val Glu Phe Leu Pro Val Gln Glu Thr
215                 220                 225                 230 cag aac gat gcg aac gac gtg gtg ccc aac tcg gat gcg aac cag aat     816
Gln Asn Asp Ala Asn Asp Val Val Pro Asn Ser Asp Ala Asn Gln Asn
                235                 240                 245
```

-continued

| | | |
|---|---|---|
| tac tgg ggc tac atg acc gag aac tat ttt tcg ccc gat cgg cgc tac<br>Tyr Trp Gly Tyr Met Thr Glu Asn Tyr Phe Ser Pro Asp Arg Arg Tyr<br>250             255                 260 | 864 |
| gcc tat aac aag gca ccg ggc ggc ccc acg gcg gaa ttc cgg gcg atg<br>Ala Tyr Asn Lys Ala Pro Gly Gly Pro Thr Ala Glu Phe Arg Ala Met<br>265             270                 275 | 912 |
| gtg cag gcg ttc cac aat gcc ggc atc aag gtc tat atg gac gtg gtc<br>Val Gln Ala Phe His Asn Ala Gly Ile Lys Val Tyr Met Asp Val Val<br>280             285                 290 | 960 |
| tac aac cac acc gcc gaa ggt ggc acc tgg acg agc aac gat ccc acc<br>Tyr Asn His Thr Ala Glu Gly Gly Thr Trp Thr Ser Asn Asp Pro Thr<br>295             300                 305                 310 | 1008 |
| acg gcg acc atc tac tcg tgg cgt ggc ctg gac aac ggc acc tat tac<br>Thr Ala Thr Ile Tyr Ser Trp Arg Gly Leu Asp Asn Gly Thr Tyr Tyr<br>315             320                 325 | 1056 |
| gaa ctc acc tcc gac cat caa tac ttc tac gac aac acc ggc acc ggc<br>Glu Leu Thr Ser Asp His Gln Tyr Phe Tyr Asp Asn Thr Gly Thr Gly<br>330             335                 340 | 1104 |
| gcg aac ttc aac acc tac aac acg gtg gcg cag aac ctg atc gtg gat<br>Ala Asn Phe Asn Thr Tyr Asn Thr Val Ala Gln Asn Leu Ile Val Asp<br>345             350                 355 | 1152 |
| tcg ctg gcc tat tgg gcg aac acg atg ggc gtg gac ggc ttc cgc ttc<br>Ser Leu Ala Tyr Trp Ala Asn Thr Met Gly Val Asp Gly Phe Arg Phe<br>360             365                 370 | 1200 |
| gat ctc gcc tcg gtg ctg ggc aat agc tgc ctc aat ggt gcg tat acc<br>Asp Leu Ala Ser Val Leu Gly Asn Ser Cys Leu Asn Gly Ala Tyr Thr<br>375             380                 385                 390 | 1248 |
| gcc tcg gcg ccg aac tgc ccg aac ggc ggt tac aac ttc gac gcg gcc<br>Ala Ser Ala Pro Asn Cys Pro Asn Gly Gly Tyr Asn Phe Asp Ala Ala<br>395             400                 405 | 1296 |
| gac agc aac gtg gcg atc aac cgc atc ctg cgc gag ttc acc gtg cgt<br>Asp Ser Asn Val Ala Ile Asn Arg Ile Leu Arg Glu Phe Thr Val Arg<br>410             415                 420 | 1344 |
| ccc gcc gct ggc ggc agc ggt ctg gat ctg ttt gcc gag ccg tgg gcg<br>Pro Ala Ala Gly Gly Ser Gly Leu Asp Leu Phe Ala Glu Pro Trp Ala<br>425             430                 435 | 1392 |
| atc aat ggc aat tcc tac cag ctc ggc ggt ttt ccg cag gga tgg tcg<br>Ile Asn Gly Asn Ser Tyr Gln Leu Gly Gly Phe Pro Gln Gly Trp Ser<br>440             445                 450 | 1440 |
| gag tgg aac ggc ttg ttc cgc gac agc ctg cgt cag gcg cag aac gaa<br>Glu Trp Asn Gly Leu Phe Arg Asp Ser Leu Arg Gln Ala Gln Asn Glu<br>455             460                 465                 470 | 1488 |
| ctg ggc agc acg acc atc cac atc acc cag gac gcg aac gac ttc tcc<br>Leu Gly Ser Thr Thr Ile His Ile Thr Gln Asp Ala Asn Asp Phe Ser<br>475             480                 485 | 1536 |
| ggt tcg tcc aac ctg ttc cag gcg aac gga cgc gcg ccg tgg aac tcg<br>Gly Ser Ser Asn Leu Phe Gln Ala Asn Gly Arg Ala Pro Trp Asn Ser<br>490             495                 500 | 1584 |
| gtg aac ttc atc gat gtg cac gac ggc ctg acc ttg aac gac gtc tat<br>Val Asn Phe Ile Asp Val His Asp Gly Leu Thr Leu Asn Asp Val Tyr<br>505             510                 515 | 1632 |
| tcg tgc aat ggc gcc aac aac agc cag gcg tgg ccg tac ggt ccg tcg<br>Ser Cys Asn Gly Ala Asn Asn Ser Gln Ala Trp Pro Tyr Gly Pro Ser<br>520             525                 530 | 1680 |
| gac ggc ggc acc agc acc aat tac agc tgg gac cag ggc atg tcc gcc<br>Asp Gly Gly Thr Ser Thr Asn Tyr Ser Trp Asp Gln Gly Met Ser Ala<br>535             540                 545                 550 | 1728 |
| ggc acc ggc acg gcg ttc gat cag cgt cgc gct gcg cgc acg ggc atg<br>Gly Thr Gly Thr Ala Phe Asp Gln Arg Arg Ala Ala Arg Thr Gly Met<br>555             560                 565 | 1776 |

-continued

```
gct ttc gag atg ctc tcg gca ggc acg ccg ctg atg cag ggt ggc gat    1824
Ala Phe Glu Met Leu Ser Ala Gly Thr Pro Leu Met Gln Gly Gly Asp
        570                 575                 580 gaa cac ctg cgc acg ctc aag tgc aac aac aac gcc tac aac ctc gat    1872
Glu His Leu Arg Thr Leu Lys Cys Asn Asn Asn Ala Tyr Asn Leu Asp
585                 590                 595 tcc agc gcg aac tgg ctc agc agc agc tgg act acc gac cag acc aac    1920
Ser Ser Ala Asn Trp Leu Ser Ser Ser Trp Thr Thr Asp Gln Thr Asn
        600                 605                 610 ttc tac acc tat gcc cag cgc ctg atc gcc ttc cgc aag gcg cat ccc    1968
Phe Tyr Thr Tyr Ala Gln Arg Leu Ile Ala Phe Arg Lys Ala His Pro
615                 620                 625                 630 gcg ttg cgt ccc gcc acc tgg tac acc gcc agc cag ctg gtg tgg tac    2016
Ala Leu Arg Pro Ala Thr Trp Tyr Thr Ala Ser Gln Leu Val Trp Tyr
                635                 640                 645 cag ccc agc ggc gca acc gcg gat acc aat tac tgg aac aac acc agc    2064
Gln Pro Ser Gly Ala Thr Ala Asp Thr Asn Tyr Trp Asn Asn Thr Ser
            650                 655                 660 aac tac gcg ctt gcc tac acc atc aac ggt cca tcg ttg ggt gac agc    2112
Asn Tyr Ala Leu Ala Tyr Thr Ile Asn Gly Pro Ser Leu Gly Asp Ser
        665                 670                 675 aac tcg atc tat gtc gct tac aac ggc tgg tcc ggc agt gtc acc ttc    2160
Asn Ser Ile Tyr Val Ala Tyr Asn Gly Trp Ser Gly Ser Val Thr Phe
    680                 685                 690 acg ctg ccg gcg cca ccc tcg ggc acg cag tgg tat cgc gtc acc gat    2208
Thr Leu Pro Ala Pro Pro Ser Gly Thr Gln Trp Tyr Arg Val Thr Asp
695                 700                 705                 710 acc tgc aac tgg aac gac ggc gcc aat acg ttc gtt gct ccc ggc agc    2256
Thr Cys Asn Trp Asn Asp Gly Ala Asn Thr Phe Val Ala Pro Gly Ser
                715                 720                 725 gag acc ctg atc ggc ggg gca ggc acc acc tat gga cag tgc ggc cag    2304
Glu Thr Leu Ile Gly Gly Ala Gly Thr Thr Tyr Gly Gln Cys Gly Gln
            730                 735                 740 tcg ctg ttg ctg ctg atc tcc aag                                    2328
Ser Leu Leu Leu Leu Ile Ser Lys
        745                 750

<210> SEQ ID NO 6
<211> LENGTH: 776
<212> TYPE: PRT
<213> ORGANISM: Dyella japonica

<400> SEQUENCE: 6

Met Lys Cys Pro Lys Ile Leu Ala Ala Leu Leu Ala Cys Ala Val Leu
    -25                 -20                 -15

Ala Ala Val Pro Ala Thr Pro Val His Ala Ala Ile Asn Ser Met Ser
-10                  -5                  -1   1                5

Leu Gly Ala Ser Tyr Asn Ala Ala Gln Thr Ser Ile Thr Phe Arg Val
            10                  15                  20

Tyr Ser Ser Thr Ala Thr Arg Leu Val Leu Tyr Val Tyr Ser Ala Gly
        25                  30                  35

Tyr Gly Val Gln Glu Ser Ala Thr Tyr Pro Leu Thr Ser Val Gly Ser
    40                  45                  50

Gly Val Trp Ala Val Thr Val Pro Val Ser Ser Ile Gln Ala Ala Gly
55                  60                  65                  70

Ile Thr Gly Ser Val Tyr Tyr Gly Tyr Arg Ala Trp Gly Pro Asn Trp
                75                  80                  85

Pro Tyr Asn Ser Ser Trp Gly Lys Gly Ser Gln Ala Gly Phe Val Ser
            90                  95                  100
```

-continued

```
Asp Val Asp Ala Ser Gly Asn Arg Phe Asn Pro Asn Lys Leu Leu Leu
        105                 110                 115
Asp Pro Tyr Ala Gln Glu Val Ser Gln Asp Pro Gln Asn Pro Ser Asn
        120                 125                 130
Gln Asn Gly Asn Val Phe Ala Ser Gly Ala Ser Tyr Arg Thr Thr Asp
135                 140                 145                 150
Ser Gly Ile Tyr Ala Pro Lys Gly Val Val Leu Ala Pro Ile Thr Gln
                155                 160                 165
Ser Thr Gly Ser Lys Pro Thr Arg Ala Gln Lys Asp Asp Val Ile Tyr
                170                 175                 180
Glu Val His Val Arg Gly Phe Thr Glu Gln Asp Ser Ser Ile Ala Ala
            185                 190                 195
Gln Tyr Arg Gly Thr Tyr Tyr Gly Ala Gly Leu Lys Ala Ser Tyr Leu
        200                 205                 210
Ala Ser Leu Gly Val Thr Ala Val Glu Phe Leu Pro Val Gln Glu Thr
215                 220                 225                 230
Gln Asn Asp Ala Asn Asp Val Val Pro Asn Ser Asp Ala Asn Gln Asn
                235                 240                 245
Tyr Trp Gly Tyr Met Thr Glu Asn Tyr Phe Ser Pro Asp Arg Arg Tyr
            250                 255                 260
Ala Tyr Asn Lys Ala Pro Gly Gly Pro Thr Ala Glu Phe Arg Ala Met
        265                 270                 275
Val Gln Ala Phe His Asn Ala Gly Ile Lys Val Tyr Met Asp Val Val
        280                 285                 290
Tyr Asn His Thr Ala Glu Gly Gly Thr Trp Thr Ser Asn Asp Pro Thr
295                 300                 305                 310
Thr Ala Thr Ile Tyr Ser Trp Arg Gly Leu Asp Asn Gly Thr Tyr Tyr
                315                 320                 325
Glu Leu Thr Ser Asp His Gln Tyr Phe Tyr Asp Asn Thr Gly Thr Gly
                330                 335                 340
Ala Asn Phe Asn Thr Tyr Asn Thr Val Ala Gln Asn Leu Ile Val Asp
            345                 350                 355
Ser Leu Ala Tyr Trp Ala Asn Thr Met Gly Val Asp Gly Phe Arg Phe
        360                 365                 370
Asp Leu Ala Ser Val Leu Gly Asn Ser Cys Leu Asn Gly Ala Tyr Thr
375                 380                 385                 390
Ala Ser Ala Pro Asn Cys Pro Asn Gly Gly Tyr Asn Phe Asp Ala Ala
                395                 400                 405
Asp Ser Asn Val Ala Ile Asn Arg Ile Leu Arg Glu Phe Thr Val Arg
            410                 415                 420
Pro Ala Ala Gly Gly Ser Gly Leu Asp Leu Phe Ala Glu Pro Trp Ala
        425                 430                 435
Ile Asn Gly Asn Ser Tyr Gln Leu Gly Gly Phe Pro Gln Gly Trp Ser
440                 445                 450
Glu Trp Asn Gly Leu Phe Arg Asp Ser Leu Arg Gln Ala Gln Asn Glu
455                 460                 465                 470
Leu Gly Ser Thr Thr Ile His Ile Thr Gln Asp Ala Asn Asp Phe Ser
                475                 480                 485
Gly Ser Ser Asn Leu Phe Gln Ala Asn Gly Arg Ala Pro Trp Asn Ser
                490                 495                 500
Val Asn Phe Ile Asp Val His Asp Gly Leu Thr Leu Asn Asp Val Tyr
            505                 510                 515
Ser Cys Asn Gly Ala Asn Asn Ser Gln Ala Trp Pro Tyr Gly Pro Ser
```

-continued

```
                520                 525                 530
Asp Gly Gly Thr Ser Thr Asn Tyr Ser Trp Asp Gln Gly Met Ser Ala
535                 540                 545                 550

Gly Thr Gly Thr Ala Phe Asp Gln Arg Arg Ala Ala Arg Thr Gly Met
                555                 560                 565

Ala Phe Glu Met Leu Ser Ala Gly Thr Pro Leu Met Gln Gly Gly Asp
                570                 575                 580

Glu His Leu Arg Thr Leu Lys Cys Asn Asn Ala Tyr Asn Leu Asp
                585                 590                 595

Ser Ser Ala Asn Trp Leu Ser Ser Ser Trp Thr Thr Asp Gln Thr Asn
                600                 605                 610

Phe Tyr Thr Tyr Ala Gln Arg Leu Ile Ala Phe Arg Lys Ala His Pro
615                 620                 625                 630

Ala Leu Arg Pro Ala Thr Trp Tyr Thr Ala Ser Gln Leu Val Trp Tyr
                635                 640                 645

Gln Pro Ser Gly Ala Thr Ala Asp Thr Asn Tyr Trp Asn Asn Thr Ser
                650                 655                 660

Asn Tyr Ala Leu Ala Tyr Thr Ile Asn Gly Pro Ser Leu Gly Asp Ser
                665                 670                 675

Asn Ser Ile Tyr Val Ala Tyr Asn Gly Trp Ser Gly Ser Val Thr Phe
                680                 685                 690

Thr Leu Pro Ala Pro Pro Ser Gly Thr Gln Trp Tyr Arg Val Thr Asp
695                 700                 705                 710

Thr Cys Asn Trp Asn Asp Gly Ala Asn Thr Phe Val Ala Pro Gly Ser
                715                 720                 725

Glu Thr Leu Ile Gly Gly Ala Gly Thr Thr Tyr Gly Gln Cys Gly Gln
                730                 735                 740

Ser Leu Leu Leu Leu Ile Ser Lys
                745                 750

<210> SEQ ID NO 7
<211> LENGTH: 2328
<212> TYPE: DNA
<213> ORGANISM: Dyella japonica
<220> FEATURE:
<221> NAME/KEY: CDS
<222> LOCATION: (1)..(2328)
<220> FEATURE:
<221> NAME/KEY: sig_peptide
<222> LOCATION: (1)..(78)
<220> FEATURE:
<221> NAME/KEY: mat_peptide
<222> LOCATION: (79)..(2328)

<400> SEQUENCE: 7 atg aag tgc tcg aag att ctc gcc gcc cta ctg gta ggt gcg agc ctg      48
Met Lys Cys Ser Lys Ile Leu Ala Ala Leu Leu Val Gly Ala Ser Leu
    -25                 -20                 -15 gcc gtt gcg ccc atg atg cct gcc cat gca gcc atc aac agc atg ggc      96
Ala Val Ala Pro Met Met Pro Ala His Ala Ala Ile Asn Ser Met Gly
-10                  -5                  -1  1               5 ctt ggc gcc agc tac aac tcg cag aaa acc agt gtt acg ttt cag gtc     144
Leu Gly Ala Ser Tyr Asn Ser Gln Lys Thr Ser Val Thr Phe Gln Val
                10                  15                  20 tat tcc tcg caa gcc acg cgc atg gtg ctt tac ctc tat gcc agc ggt     192
Tyr Ser Ser Gln Ala Thr Arg Met Val Leu Tyr Leu Tyr Ala Ser Gly
            25                  30                  35 tac ggc gca cag gaa tcg acg acc tat gtg ctc agc cca caa ggc aac     240
Tyr Gly Ala Gln Glu Ser Thr Thr Tyr Val Leu Ser Pro Gln Gly Asn
        40                  45                  50
```

```
ggc gtc tgg tcg gta acc gtg cct gtg tct gcc atc cag gcg gca ggc    288
Gly Val Trp Ser Val Thr Val Pro Val Ser Ala Ile Gln Ala Ala Gly
 55              60              65              70 att acc ggt tcg atc tac tac ggc tat cgc gcc tgg ggg ccc aac tgg    336
Ile Thr Gly Ser Ile Tyr Tyr Gly Tyr Arg Ala Trp Gly Pro Asn Trp
             75              80              85 ccg tat aac gcg agc tgg ggc aaa ggg tcc cag gcg ggc ttt gtt tcg    384
Pro Tyr Asn Ala Ser Trp Gly Lys Gly Ser Gln Ala Gly Phe Val Ser
         90              95             100 gac gtc gat gcc aat ggc aat cgc ttc aat ccc aac aaa ctg ttg ctg    432
Asp Val Asp Ala Asn Gly Asn Arg Phe Asn Pro Asn Lys Leu Leu Leu
            105             110             115 gac ccc tac gcg cag gaa atg agc cag gat ccg ctc aac cct tcg aat    480
Asp Pro Tyr Ala Gln Glu Met Ser Gln Asp Pro Leu Asn Pro Ser Asn
        120             125             130 cag aac ggc aac gtg ttc gcc tcg ggt gcc agc tac cgc aac atc gac    528
Gln Asn Gly Asn Val Phe Ala Ser Gly Ala Ser Tyr Arg Asn Ile Asp
135             140             145             150 agc ggt acg tac gca ccc aag ggc atc gtg ctg gcc ccc agt acg cag    576
Ser Gly Thr Tyr Ala Pro Lys Gly Ile Val Leu Ala Pro Ser Thr Gln
                155             160             165 agc aca ggc acc aag ccc acg cgc gcg caa aag gac gac gtc atc tac    624
Ser Thr Gly Thr Lys Pro Thr Arg Ala Gln Lys Asp Asp Val Ile Tyr
            170             175             180 gag gtg aac gtg cgt ggc ttc acc aag cag gac ccg agc ata gcc acg    672
Glu Val Asn Val Arg Gly Phe Thr Lys Gln Asp Pro Ser Ile Ala Thr
        185             190             195 gcc tat cag ggc act tat tac ggt gcc ggg ctc aag gcc agc tac ctc    720
Ala Tyr Gln Gly Thr Tyr Tyr Gly Ala Gly Leu Lys Ala Ser Tyr Leu
200             205             210 gca agc ctc ggc gtg acc gcg gtg gaa ttc ctg ccg gtg cag gaa acg    768
Ala Ser Leu Gly Val Thr Ala Val Glu Phe Leu Pro Val Gln Glu Thr
215             220             225             230 cag aac gat gcc aac gat gtc gtc gcc aat tcg gat gcg aac cag aac    816
Gln Asn Asp Ala Asn Asp Val Val Ala Asn Ser Asp Ala Asn Gln Asn
            235             240             245 tac tgg ggc tat atg acc gaa gac tac ttc gcc ccg gac cgt cgc tat    864
Tyr Trp Gly Tyr Met Thr Glu Asp Tyr Phe Ala Pro Asp Arg Arg Tyr
        250             255             260 gcg tac aac aag gcg cct ggc gga ccc acg gcc gaa ttc cag gcg atg    912
Ala Tyr Asn Lys Ala Pro Gly Gly Pro Thr Ala Glu Phe Gln Ala Met
    265             270             275 gtg cag gcg ttc cat aat gtc ggc atc aag gtc tat atg gac gtg gtc    960
Val Gln Ala Phe His Asn Val Gly Ile Lys Val Tyr Met Asp Val Val
280             285             290 tac aac cac acc ggc gaa ggc ggt acg tgg acg agc acc gac ccc acc   1008
Tyr Asn His Thr Gly Glu Gly Gly Thr Trp Thr Ser Thr Asp Pro Thr
295             300             305             310 acg gcc acc atc tat tcg tgg cgc ggc ctg gac aat acg acg tac tac   1056
Thr Ala Thr Ile Tyr Ser Trp Arg Gly Leu Asp Asn Thr Thr Tyr Tyr
            315             320             325 gag ctc aac tcg ggc aac cag tac ttc tac gac aac acc ggt acc ggc   1104
Glu Leu Asn Ser Gly Asn Gln Tyr Phe Tyr Asp Asn Thr Gly Thr Gly
        330             335             340 gcc aat ttc aac acc tac aac acg gtg gcc cag aat ctg atc gtc gac   1152
Ala Asn Phe Asn Thr Tyr Asn Thr Val Ala Gln Asn Leu Ile Val Asp
    345             350             355 tcg ctg gcc tac tgg gcc aac acc atg ggc gtc gac ggc ttt cgc ttc   1200
Ser Leu Ala Tyr Trp Ala Asn Thr Met Gly Val Asp Gly Phe Arg Phe
360             365             370
```

```
gac ctc gcc tcg gtg ctt ggc aat agc tgc ctg aat gcc aat gcc gtt    1248
Asp Leu Ala Ser Val Leu Gly Asn Ser Cys Leu Asn Ala Asn Ala Val
375                 380                 385                 390 gca gct gcg ccg aac tgc ccg aac ggc ggc tac aac ttc gac gcg gcc    1296
Ala Ala Ala Pro Asn Cys Pro Asn Gly Gly Tyr Asn Phe Asp Ala Ala
                395                 400                 405 gat tcg aat gtc gcc atc aac cgc atc ctg cgt gaa ttc acc gtg cgc    1344
Asp Ser Asn Val Ala Ile Asn Arg Ile Leu Arg Glu Phe Thr Val Arg
        410                 415                 420 ccg gcc gcc ggt ggc agc ggc ctg gat ctg ttt gcc gaa ccg tgg gcg    1392
Pro Ala Ala Gly Gly Ser Gly Leu Asp Leu Phe Ala Glu Pro Trp Ala
425                 430                 435 att ggt ggc aat tcc tac cag ctc ggc ggt ttc ccg cca ggt tgg tcg    1440
Ile Gly Gly Asn Ser Tyr Gln Leu Gly Gly Phe Pro Pro Gly Trp Ser
        440                 445                 450 gaa tgg aat ggt gta ttc cgt gac agc ttc cgt cag gcg caa aac gag    1488
Glu Trp Asn Gly Val Phe Arg Asp Ser Phe Arg Gln Ala Gln Asn Glu
455                 460                 465                 470 ctg ggc aat atg gcc att tcc att ggc cag gac gcg acg aac ttt tcc    1536
Leu Gly Asn Met Ala Ile Ser Ile Gly Gln Asp Ala Thr Asn Phe Ser
                475                 480                 485 ggc tca tcc aac ctg ttt caa gcc agt ggt cgt gcg ccc tgg aat tcg    1584
Gly Ser Ser Asn Leu Phe Gln Ala Ser Gly Arg Ala Pro Trp Asn Ser
        490                 495                 500 acg aac ttt atc gat gtg cat gac ggc atg acg ctc aag gac gtc tat    1632
Thr Asn Phe Ile Asp Val His Asp Gly Met Thr Leu Lys Asp Val Tyr
505                 510                 515 tcg tgc aac ggt gcc agc aac agc cag gca tgg cct tat ggt cca tcc    1680
Ser Cys Asn Gly Ala Ser Asn Ser Gln Ala Trp Pro Tyr Gly Pro Ser
        520                 525                 530 gat ggc ggc acc agc acc aac tac agc tgg gat cag ggc atg tcg gcg    1728
Asp Gly Gly Thr Ser Thr Asn Tyr Ser Trp Asp Gln Gly Met Ser Ala
535                 540                 545                 550 ggc acg ggc acc gcg gtc gac caa cgg cgt gcg gcg cgc acc ggc atg    1776
Gly Thr Gly Thr Ala Val Asp Gln Arg Arg Ala Ala Arg Thr Gly Met
                555                 560                 565 gcc ttc gaa atg ctg tcg gcc gga acg ccg ctg atg caa ggt ggc gat    1824
Ala Phe Glu Met Leu Ser Ala Gly Thr Pro Leu Met Gln Gly Gly Asp
        570                 575                 580 gaa tac ctg cgc acg ctt cag tgc aac aac aac gcg tac aac ctc gac    1872
Glu Tyr Leu Arg Thr Leu Gln Cys Asn Asn Asn Ala Tyr Asn Leu Asp
585                 590                 595 tcc agc gcg aac tgg ctc agc tac agc tgg acc acg gac cag tcg aac    1920
Ser Ser Ala Asn Trp Leu Ser Tyr Ser Trp Thr Thr Asp Gln Ser Asn
        600                 605                 610 ttc tac aac ttc gcg cag cgg ctg atc gcc ttc cgc aag gcg cat cct    1968
Phe Tyr Asn Phe Ala Gln Arg Leu Ile Ala Phe Arg Lys Ala His Pro
615                 620                 625                 630 gcc ctt cga cct gct acc tgg tac agc acc agc cag gtg gtg tgg tat    2016
Ala Leu Arg Pro Ala Thr Trp Tyr Ser Thr Ser Gln Val Val Trp Tyr
                635                 640                 645 cag cca agc ggc gct gtc gct acc agc agt tac tgg agc aac agc agc    2064
Gln Pro Ser Gly Ala Val Ala Thr Ser Ser Tyr Trp Ser Asn Ser Ser
        650                 655                 660 aat tac gcg ctc gcc tat acc gtc aac gga ccc tcg ctg ggc gat acc    2112
Asn Tyr Ala Leu Ala Tyr Thr Val Asn Gly Pro Ser Leu Gly Asp Thr
665                 670                 675 aac tcg atg tat atc gcc tat aac ggc tgg tcg ggc agc gtc acc ttc    2160
Asn Ser Met Tyr Ile Ala Tyr Asn Gly Trp Ser Gly Ser Val Thr Phe
        680                 685                 690
```

-continued

```
acc ctg ccg gcg ccg ccg tcg ggc acc agc tgg tat cgg gtc acg gat    2208
Thr Leu Pro Ala Pro Pro Ser Gly Thr Ser Trp Tyr Arg Val Thr Asp
695             700                 705                 710 acc tgc gac tgg aat gat ggc gcc aat acc ttc gtt acc ccg ggc aac    2256
Thr Cys Asp Trp Asn Asp Gly Ala Asn Thr Phe Val Thr Pro Gly Asn
            715                 720                 725 gag gca tcg att ggc ggt gca ggc acc acc tac agc cag tgt ggc cag    2304
Glu Ala Ser Ile Gly Gly Ala Gly Thr Thr Tyr Ser Gln Cys Gly Gln
        730                 735                 740 tct ttg ttg ttg ctg atc tcg aag                                    2328
Ser Leu Leu Leu Leu Ile Ser Lys
            745                 750

<210> SEQ ID NO 8
<211> LENGTH: 776
<212> TYPE: PRT
<213> ORGANISM: Dyella japonica

<400> SEQUENCE: 8

Met Lys Cys Ser Lys Ile Leu Ala Ala Leu Leu Val Gly Ala Ser Leu
    -25                 -20                 -15

Ala Val Ala Pro Met Met Pro Ala His Ala Ala Ile Asn Ser Met Gly
-10                  -5              -1   1                   5

Leu Gly Ala Ser Tyr Asn Ser Gln Lys Thr Ser Val Thr Phe Gln Val
                10                  15                  20

Tyr Ser Ser Gln Ala Thr Arg Met Val Leu Tyr Leu Tyr Ala Ser Gly
            25                  30                  35

Tyr Gly Ala Gln Glu Ser Thr Thr Tyr Val Leu Ser Pro Gln Gly Asn
        40                  45                  50

Gly Val Trp Ser Val Thr Val Pro Val Ser Ala Ile Gln Ala Ala Gly
55                  60                  65                  70

Ile Thr Gly Ser Ile Tyr Tyr Gly Tyr Arg Ala Trp Gly Pro Asn Trp
                75                  80                  85

Pro Tyr Asn Ala Ser Trp Gly Lys Gly Ser Gln Ala Gly Phe Val Ser
            90                  95                  100

Asp Val Asp Ala Asn Gly Asn Arg Phe Asn Pro Asn Lys Leu Leu Leu
        105                 110                 115

Asp Pro Tyr Ala Gln Glu Met Ser Gln Asp Pro Leu Asn Pro Ser Asn
120                 125                 130

Gln Asn Gly Asn Val Phe Ala Ser Gly Ala Ser Tyr Arg Asn Ile Asp
135                 140                 145                 150

Ser Gly Thr Tyr Ala Pro Lys Gly Ile Val Leu Ala Pro Ser Thr Gln
                155                 160                 165

Ser Thr Gly Thr Lys Pro Thr Arg Ala Gln Lys Asp Asp Val Ile Tyr
            170                 175                 180

Glu Val Asn Val Arg Gly Phe Thr Lys Gln Asp Pro Ser Ile Ala Thr
        185                 190                 195

Ala Tyr Gln Gly Thr Tyr Tyr Gly Ala Gly Leu Lys Ala Ser Tyr Leu
200                 205                 210

Ala Ser Leu Gly Val Thr Ala Val Glu Phe Leu Pro Val Gln Glu Thr
215                 220                 225                 230

Gln Asn Asp Ala Asn Asp Val Val Ala Asn Ser Asp Ala Asn Gln Asn
                235                 240                 245

Tyr Trp Gly Tyr Met Thr Glu Asp Tyr Phe Ala Pro Asp Arg Arg Tyr
            250                 255                 260

Ala Tyr Asn Lys Ala Pro Gly Gly Pro Thr Ala Glu Phe Gln Ala Met
```

-continued

```
                265                 270                 275
Val Gln Ala Phe His Asn Val Gly Ile Lys Val Tyr Met Asp Val Val
            280                 285                 290
Tyr Asn His Thr Gly Glu Gly Gly Thr Trp Thr Ser Thr Asp Pro Thr
295                 300                 305                 310
Thr Ala Thr Ile Tyr Ser Trp Arg Gly Leu Asp Asn Thr Thr Tyr Tyr
                315                 320                 325
Glu Leu Asn Ser Gly Asn Gln Tyr Phe Tyr Asp Asn Thr Gly Thr Gly
            330                 335                 340
Ala Asn Phe Asn Thr Tyr Asn Thr Val Ala Gln Asn Leu Ile Val Asp
            345                 350                 355
Ser Leu Ala Tyr Trp Ala Asn Thr Met Gly Val Asp Gly Phe Arg Phe
        360                 365                 370
Asp Leu Ala Ser Val Leu Gly Asn Ser Cys Leu Asn Ala Asn Ala Val
375                 380                 385                 390
Ala Ala Ala Pro Asn Cys Pro Asn Gly Gly Tyr Asn Phe Asp Ala Ala
                395                 400                 405
Asp Ser Asn Val Ala Ile Asn Arg Ile Leu Arg Glu Phe Thr Val Arg
            410                 415                 420
Pro Ala Ala Gly Gly Ser Gly Leu Asp Leu Phe Ala Glu Pro Trp Ala
        425                 430                 435
Ile Gly Gly Asn Ser Tyr Gln Leu Gly Gly Phe Pro Pro Gly Trp Ser
        440                 445                 450
Glu Trp Asn Gly Val Phe Arg Asp Ser Phe Arg Gln Ala Gln Asn Glu
455                 460                 465                 470
Leu Gly Asn Met Ala Ile Ser Ile Gly Gln Asp Ala Thr Asn Phe Ser
                475                 480                 485
Gly Ser Ser Asn Leu Phe Gln Ala Ser Gly Arg Ala Pro Trp Asn Ser
            490                 495                 500
Thr Asn Phe Ile Asp Val His Asp Gly Met Thr Leu Lys Asp Val Tyr
            505                 510                 515
Ser Cys Asn Gly Ala Ser Asn Ser Gln Ala Trp Pro Tyr Gly Pro Ser
        520                 525                 530
Asp Gly Gly Thr Ser Thr Asn Tyr Ser Trp Asp Gln Gly Met Ser Ala
535                 540                 545                 550
Gly Thr Gly Thr Ala Val Asp Gln Arg Arg Ala Ala Arg Thr Gly Met
                555                 560                 565
Ala Phe Glu Met Leu Ser Ala Gly Thr Pro Leu Met Gln Gly Gly Asp
            570                 575                 580
Glu Tyr Leu Arg Thr Leu Gln Cys Asn Asn Asn Ala Tyr Asn Leu Asp
            585                 590                 595
Ser Ser Ala Asn Trp Leu Ser Tyr Ser Trp Thr Thr Asp Gln Ser Asn
        600                 605                 610
Phe Tyr Asn Phe Ala Gln Arg Leu Ile Ala Phe Arg Lys Ala His Pro
615                 620                 625                 630
Ala Leu Arg Pro Ala Thr Trp Tyr Ser Thr Ser Gln Val Val Trp Tyr
                635                 640                 645
Gln Pro Ser Gly Ala Val Ala Thr Ser Ser Tyr Trp Ser Asn Ser Ser
            650                 655                 660
Asn Tyr Ala Leu Ala Tyr Thr Val Asn Gly Pro Ser Leu Gly Asp Thr
            665                 670                 675
Asn Ser Met Tyr Ile Ala Tyr Asn Gly Trp Ser Gly Ser Val Thr Phe
        680                 685                 690
```

```
Thr Leu Pro Ala Pro Pro Ser Gly Thr Ser Trp Tyr Arg Val Thr Asp
695                 700                 705                 710

Thr Cys Asp Trp Asn Asp Gly Ala Asn Thr Phe Val Thr Pro Gly Asn
            715                 720                 725

Glu Ala Ser Ile Gly Gly Ala Gly Thr Thr Tyr Ser Gln Cys Gly Gln
        730                 735                 740

Ser Leu Leu Leu Leu Ile Ser Lys
        745                 750

<210> SEQ ID NO 9
<211> LENGTH: 46
<212> TYPE: DNA
<213> ORGANISM: Artificial Sequence
<220> FEATURE:
<223> OTHER INFORMATION: synthetic construct

<400> SEQUENCE: 9
cttgctgcct cattctgcag ccgcggccat caacagcatg accttg                46

<210> SEQ ID NO 10
<211> LENGTH: 50
<212> TYPE: DNA
<213> ORGANISM: Artificial Sequence
<220> FEATURE:
<223> OTHER INFORMATION: synthetic construct

<400> SEQUENCE: 10
gggccaaggc cggttttta tgttttactt cgaaatcaac aacaacagcg            50

<210> SEQ ID NO 11
<211> LENGTH: 49
<212> TYPE: DNA
<213> ORGANISM: Artificial Sequence
<220> FEATURE:
<223> OTHER INFORMATION: synthetic construct

<400> SEQUENCE: 11
cttgctgcct cattctgcag ccgcgacacc ggcccaggcg gccatcaac             49

<210> SEQ ID NO 12
<211> LENGTH: 56
<212> TYPE: DNA
<213> ORGANISM: Artificial Sequence
<220> FEATURE:
<223> OTHER INFORMATION: synthetic construct

<400> SEQUENCE: 12
gggccaaggc cggttttta tgttttactt ggaaatcagc agcagcaacg actggc     56

<210> SEQ ID NO 13
<211> LENGTH: 47
<212> TYPE: DNA
<213> ORGANISM: Artificial Sequence
<220> FEATURE:
<223> OTHER INFORMATION: synthetic construct

<400> SEQUENCE: 13
cttgctgcct cattctgcag ccgcggccat caacagcatg agtcttg               47

<210> SEQ ID NO 14
<211> LENGTH: 49
<212> TYPE: DNA
<213> ORGANISM: Artificial Sequence
<220> FEATURE:
<223> OTHER INFORMATION: synthetic construct
```

```
<400> SEQUENCE: 14
gggccaaggc cggttttta tgttttactt ggagatcagc agcaacagc              49

<210> SEQ ID NO 15
<211> LENGTH: 45
<212> TYPE: DNA
<213> ORGANISM: Artificial Sequence
<220> FEATURE:
<223> OTHER INFORMATION: synthetic construct

<400> SEQUENCE: 15
cttgctgcct cattctgcag ccgcggccat caacagcatg ggcct              45

<210> SEQ ID NO 16
<211> LENGTH: 54
<212> TYPE: DNA
<213> ORGANISM: Artificial Sequence
<220> FEATURE:
<223> OTHER INFORMATION: synthetic construct

<400> SEQUENCE: 16
gggccaaggc cggttttta tgttttactt cgagatcagc aacaacaaag actg          54

<210> SEQ ID NO 17
<211> LENGTH: 15
<212> TYPE: DNA
<213> ORGANISM: Artificial Sequence
<220> FEATURE:
<223> OTHER INFORMATION: synthetic construct

<400> SEQUENCE: 17
acaatatgcg ggacg                                              15

<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
cgcggctgca gaatgaggca                                         20

<210> SEQ ID NO 19
<211> LENGTH: 25
<212> TYPE: DNA
<213> ORGANISM: Artificial Sequence
<220> FEATURE:
<223> OTHER INFORMATION: synthetic construct

<400> SEQUENCE: 19
taaaacataa aaaccggcc ttggc                                    25

<210> SEQ ID NO 20
<211> LENGTH: 15
<212> TYPE: DNA
<213> ORGANISM: Artificial Sequence
<220> FEATURE:
<223> OTHER INFORMATION: synthetic construct

<400> SEQUENCE: 20
gacatcagcc ctgct                                              15

<210> SEQ ID NO 21
<211> LENGTH: 4
<212> TYPE: PRT
```

```
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Glu or Asp

<400> SEQUENCE: 21

Ile Xaa Gly Arg
1

<210> SEQ ID NO 22
<211> LENGTH: 5
<212> TYPE: PRT
<213> ORGANISM: Artificial sequence
<220> FEATURE:
<223> OTHER INFORMATION: Synthetic construct

<400> SEQUENCE: 22

Asp Asp Asp Asp Lys
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic construct

<400> SEQUENCE: 23

Leu Val Pro Arg Gly Ser
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic construct

<400> SEQUENCE: 24

Glu Asn Leu Tyr Phe Gln Gly
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic construct

<400> SEQUENCE: 25

Leu Glu Val Leu Phe Gln Gly Pro
1               5
```

POLYPEPTIDES HAVING ISOAMYLASE ACTIVITY AND METHODS OF USE

CROSS-REFERENCE TO RELATED APPLICATIONS

This application claims priority or the benefit under 35 U.S.C. 119 of European application no. 09168390.4 filed Aug. 21, 2009 and U.S. provisional application No. 61/237,805 filed Aug. 28, 2009, the contents of which are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference. For complete information see the description.

BACKGROUND OF THE INVENTION

1. Field of the Invention

The present invention relates to isolated polypeptides having isoamylase activity and isolated polynucleotides encoding the polypeptides. The invention also relates to nucleic acid constructs, vectors, and host cells comprising the polynucleotides as well as methods of producing and using the polypeptides.

2. Description of the Related Art

Isoamylase is a debranching enzyme (E.C. 3.2.1.68) that hydrolyzes 1,6-alpha-linkages in amylopectin, glycogen, and beta-limit dextrins. Amylopectin is partially degraded by alpha-amylase which hydrolyzes the 1,4-alpha-glucosidic linkages into branched and linear oligosaccharides that results in the formation of alpha-limit dextrins. Unlike pullulanase, isoamylase has high activity towards amylopectin and glycogen and very low activity towards pullulan. Branched oligosaccharides can be hydrolyzed into linear oligosaccharides by debranching enzyme. The remaining linear oligosaccharides can be rapidly depolymerized to D-glucose by glucoamylase.

U.S. Pat. No. 4,335,208 discloses a process of saccharifying starch hydrolysate by an enzyme mixture of glucoamylase and an acidophilic isoamylase derived from *Pseudomonas amyloderamosa*.

EP 1,002,062 concerns an isoamylase from *Sulfolobus acidocaldarius* and the use thereof in a starch conversion process.

WO 2005/121305 (Novozymes) concerns a process for production of beer having a low content of carbohydrates which comprises; a) preparing a mash in the presence of enzyme activities, b) filtering the mash to obtain a wort, and, c) fermenting said wort to obtain a beer, wherein the enzyme activities comprise; an alpha-amylase, a glucoamylase and an isoamylase.

It is an object of the present invention to provide polypeptides having isoamylase activity and polynucleotides encoding the polypeptides. The invention also provides uses of said isoamylase for syrup preparation and other related applications.

SUMMARY OF THE INVENTION

The present invention relates to an isolated polypeptide having isoamylase activity, selected from the group consisting of:

(a1) a polypeptide comprising an amino acid sequence having at least 93%, preferably at least 94%, more preferably at least 95%, more preferably at least 96%, more preferably at least 97%, more preferably at least 98%, even more preferably at least 99% identity to the mature polypeptide of SEQ ID NO: 2;

(a2) a polypeptide comprising an amino acid sequence having at least 94%, preferably at least 95%, more preferably at least 96%, more preferably at least 97%, more preferably at least 98%, even more preferably at least 99% identity to the mature polypeptide of SEQ ID NO: 4;

(a3) a polypeptide comprising an amino acid sequence having at least 93%, preferably at least 94%, more preferably at least 95%, more preferably at least 96%, more preferably at least 97%, more preferably at least 98%, even more preferably at least 99% identity to the mature polypeptide of SEQ ID NO: 6;

(a4) a polypeptide comprising an amino acid sequence having at least 90%, preferably at least 91%, more preferably at least 92%, more preferably at least 93%, more preferably at least 94%, more preferably at least 95%, more preferably at least 96%, more preferably at least 97%, more preferably at least 98%, even more preferably at least 99% identity to the mature polypeptide of SEQ ID NO: 8;

(b) a polypeptide encoded by a polynucleotide that hybridizes under at least high stringency conditions with (i) the mature polypeptide coding sequence of SEQ ID NO: 1, SEQ ID NO: 3, SEQ ID NO: 5 or SEQ ID NO: 7, (ii) the genomic DNA sequence comprising the mature polypeptide coding sequence of SEQ ID NO: 1, SEQ ID NO: 3, SEQ ID NO: 5 or SEQ ID NO: 7, or (iii) a full-length complementary strand of (i) or (ii);

(c1) a polypeptide encoded by a polynucleotide comprising a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 1;

(c2) a polypeptide encoded by a polynucleotide comprising a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 3;

(c3) a polypeptide encoded by a polynucleotide comprising a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 5;

(c4) a polypeptide encoded by a polynucleotide comprising a nucleotide sequence having at least 84%, preferably at least 86%, more preferably at least 87%, more preferably at least 88%, more preferably at least 89%, more preferably at least 90%, more preferably at least 92%, even more preferably at least 95%, most preferably at least 97%, and even most preferably at least 99% identity to the mature polypeptide coding sequence of SEQ ID NO: 7; and (d) a variant comprising a substitution, deletion, and/or insertion of one or more (several) amino acids of the mature polypeptide of SEQ ID NOs: 2, 4, 6 and/or 8.

The present invention also relates to an isolated polynucleotide comprising a nucleotide sequence that encodes the polypeptide of the invention. More specifically the invention in this aspect relates to an isolated polynucleotide encoding a polypeptide having isoamylase activity, obtained by:

(a) hybridizing a population of DNA under at least high stringency conditions, preferably at least very high stringency conditions with (i) the mature polypeptide coding sequence of SEQ ID NO: 1, SEQ ID NO: 3, SEQ ID NO: 5 and/or SEQ ID NO: 7 (ii) the genomic DNA sequence comprising the mature polypeptide coding sequence of SEQ ID NO: 1, SEQ ID NO: 3, SEQ ID NO: 5 and/or SEQ ID NO: 7, or (iii) a full-length complementary strand of (i) or (ii);

(b) isolating the hybridized polynucleotide, which encodes a polypeptide having isoamylase activity.

The present invention also relates to nucleic acid constructs, recombinant expression vectors, recombinant host cells comprising the polynucleotides, and methods of producing a polypeptide having isoamylase activity.

The present invention also relates to methods of producing beer and syrups.

The present invention also relates to plants comprising an isolated polynucleotide encoding such a polypeptide having isoamylase activity.

The present invention also relates to methods of producing such a polypeptide having isoamylase activity, comprising: (a) cultivating a transgenic plant or a plant cell comprising a polynucleotide encoding such a polypeptide having isoamylase activity under conditions conducive for production of the polypeptide; and (b) recovering the polypeptide.

Definitions

Isoamylase activity: The term "isoamylase activity" is defined herein as an enzyme having glycogen alpha-1,6-glucanohydrolase activity (EC number 3.2.1.68) activity that catalyzes the hydrolysis of (1,6)-alpha-D-glucosidic branch linkages in glycogen, amylopectin and their beta-limit dextrins. For purposes of the present invention, isoamylase activity is determined according to the procedure as described in the "Materials & Methods"-section below under the heading "Determination of Isoamylase Activity Units (IAU)".

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the isoamylase activity of the mature polypeptide of SEQ ID NOS: 2, 4, 6, or 8, respectively.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE. The term "pure" is in this context used in relation to the polypeptide of the present invention and it is to be understood as an indication of how much other polypeptide material the polypeptide of the present invention is associated with.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 90% pure, preferably at least 92% pure, more preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having isoamylase activity that is in its final form following translation and any post-translational modifications, such as N-terminal processing, C-terminal truncation, glycosylation, phosphorylation, etc. In a preferred aspect, the mature polypeptide is amino acids 1 to 750 of SEQ ID NOS: 2, 4, 6 and 8, respectively, based on the SignalP v 3.0 program that predicts amino acids −26 to −1 of SEQ ID NOS: 2, 4, 6 and 8, respectively, are signal peptides.

Mature polypeptide coding sequence: The term "mature polypeptide coding sequence" is defined herein as a nucleotide sequence that encodes a mature polypeptide having isoamylase activity. In a preferred aspect, the mature polypeptide coding sequence is nucleotides 79 to 2328 of SEQ ID NOS: 1, 3, 5 and 7, respectively, based on the SignalP v 3.0 program that predicts nucleotides 1 to 78 of SEQ ID NOS: 1, 3, 5, and 7, respectively, encode signal peptides.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Dyella japonica* isoamylases (Accession Nos. DSM 22712, DSM 22713, DSM 22714, and DSM 22715), respectively.

Polypeptide fragment: The term "polypeptide fragment" is defined herein as a polypeptide having one or more (several) amino acids deleted from the amino and/or carboxyl terminus of the mature polypeptide of SEQ ID NOS: 2, 4, 6 or 8, respectively; or a homologous sequence thereof; wherein the fragment has isoamylase activity. The term "fragment thereof" used in relation to a polypeptide is in the context of the present invention to be understood as having the same meaning as "polypeptide fragment".

Subsequence: The term "subsequence" is defined herein as a nucleotide sequence having one or more (several) nucleotides deleted from the 5' and/or 3' end of the mature polypeptide coding sequence of SEQ ID NOS: 1, 3, 5 or 7, respectively; or a homologous sequence thereof; wherein the subsequence encodes a polypeptide fragment having isoamylase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis. The term "pure" is in this context used in relation to the polynucleotide of the present invention and it is to be understood as an indication of how much other polynucleotide material the polynucleotide of the present invention is associated with.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, or synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptides including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NOS: 2, 4, 6 or 8, respectively; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having isoamylase activity produced by an organism expressing a modified polynucleotide sequence of the mature polypeptide coding sequence of SEQ ID NOS: 1, 3, 5 or 7; or a homologous sequence thereof. The modified nucleotide sequence is obtained through human intervention by modification of the polynucleotide sequence disclosed in SEQ ID NOS: 1, 3, 5 and/or 7; or a homologous sequence thereof.

DETAILED DESCRIPTION OF THE INVENTION

Polypeptides Having Isoamylase Activity

In a first aspect, the present invention relates to an isolated polypeptide having isoamylase activity, selected from the group consisting of:

(a1) a polypeptide comprising an amino acid sequence having at least 93%, more preferably at least 94%, more preferably at least 95%, more preferably at least 96%, more preferably at least 97%, more preferably at least 98%, even more preferably at least 99% identity to the mature polypeptide of SEQ ID NO: 2;

(a2) a polypeptide comprising an amino acid sequence having at least 94%, more preferably at least 95%, more preferably at least 96%, more preferably at least 97%, more preferably at least 98%, even more preferably at least 99% identity to the mature polypeptide of SEQ ID NO: 4;

(a3) a polypeptide comprising an amino acid sequence having at least 93%, more preferably at least 94%, more preferably at least 95%, more preferably at least 96%, more preferably at least 97%, more preferably at least 98%, even more preferably at least 99% identity to the mature polypeptide of SEQ ID NO: 6;

(a4) a polypeptide comprising an amino acid sequence having at least 90%, preferably at least 91%, more preferably at least 92%, more preferably at least 93%, more preferably at least 94%, more preferably at least 95%, more preferably at least 96%, more preferably at least 97%, more preferably at least 98%, even more preferably at least 99% identity to the mature polypeptide of SEQ ID NO: 8;

(b) a polypeptide encoded by a polynucleotide that hybridizes under at least high stringency conditions with (i) the mature polypeptide coding sequence of SEQ ID NO: 1, SEQ ID NO: 3, SEQ ID NO: 5 and/or SEQ ID NO: 7 (ii) the genomic DNA sequence comprising the mature polypeptide coding sequence of SEQ ID NO: 1, SEQ ID NO: 3, SEQ ID NO: 5 or SEQ ID NO: 7, or (iii) a full-length complementary strand of (i) or (ii);

(c1) a polypeptide encoded by a polynucleotide comprising a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 1

(c2) a polypeptide encoded by a polynucleotide comprising a nucleotide sequence having at least 86%, preferably at least 88%, more preferably at least 90%, more preferably at least 92%, even more preferably at least 95%, most preferably at least 97%, and even most preferably at least 99% identity (hereinafter "homologous polypeptides") to the mature polypeptide coding sequence of SEQ ID NO: 3;

(c3) a polypeptide encoded by a polynucleotide comprising a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 5;

(c4) a polypeptide encoded by a polynucleotide comprising a nucleotide sequence having at least 84%, preferably at least 86%, more preferably at least 87%, more preferably at least 88%, more preferably at least 89%, more preferably at least 90%, more preferably at least 92%, even more preferably at least 95%, most preferably at least 97%, and even most preferably at least 99% identity to the mature polypeptide coding sequence of SEQ ID NO: 7; and (d) a variant comprising a substitution, deletion, and/or insertion of one or more (several) amino acids of the mature polypeptide of SEQ ID NOS: 2, 4, 6 and/or 8.

In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NOS: 2, 4, 6 and/or 8.

In one embodiment the polypeptide of the present invention comprises an amino acid sequence, wherein said amino acid sequence consists of the amino acid sequence of SEQ ID NOS: 2, 4, 6, 8 or an amino acid sequence that differs by 1-70 amino acids, such as 1-65 amino acids, or 1-60 amino acids, or 1-55 amino acids, or 1-50 amino acids, or 1-45 amino acids, or 1-40 amino acids, or 1-35 amino acids, or 1-30 amino acids, or 1-25 amino acids, or 1-20 amino acids, or 1-15 amino acids, or 1-10 amino acids, or 1-9 amino acids, or 1-8 amino acids, or 1-7 amino acids, or 1-6 amino acids, or 1-5 amino acids, or 1-4 amino acids, or 1-3 amino acids, or 1-2 amino acids or 1 amino acid from the amino acid sequence of SEQ ID NOS: 2, 4, 6 and/or 8, wherein the term "differ" means that the given number of amino acids have been substituted, deleted and/or inserted when compared to the amino acid sequence of SEQ ID NOS: 2, 4, 6, 8.

In another embodiment the polypeptide of the present invention comprises an amino acid sequence, wherein said amino acid sequence consists of the mature polypeptide of SEQ ID NOS: 2, 4, 6, and 8 and/or an amino acid sequence that differs by 1-70 amino acids, such as 1-65 amino acids, or 1-60 amino acids, or 1-55 amino acids, or 1-50 amino acids, or 1-45 amino acids, or 1-40 amino acids, or 1-35 amino acids, or 1-30 amino acids, or 1-25 amino acids, or 1-20 amino acids, or 1-15 amino acids, or 1-10 amino acids, or 1-9 amino acids, or 1-8 amino acids, or 1-7 amino acids, or 1-6 amino acids, or 1-5 amino acids, or 1-4 amino acids, or 1-3 amino acids, or 1-2 amino acids or 1 amino acid from the mature polypeptide of SEQ ID NOS: 2, 4, 6 and/or 8, wherein the term "differ" means that the given number of amino acids have been substituted, deleted and/or inserted when compared to the amino acid sequence of SEQ ID NOS: 2, 4, 6, 8.

In another embodiment the polypeptide of the present invention comprises an amino acid sequence, wherein said amino acid sequence consists of amino acids 1 to 750 of SEQ ID NOS: 2, 4, 6, 8 and/or an amino acid sequence that differs by 1-70 amino acids, such as 1-65 amino acids, or 1-60 amino acids, or 1-55 amino acids, or 1-50 amino acids, or 1-45 amino acids, or 1-40 amino acids, or 1-35 amino acids, or 1-30 amino acids, or 1-25 amino acids, or 1-20 amino acids, or 1-15 amino acids, or 1-10 amino acids, or 1-9 amino acids, or 1-8 amino acids, or 1-7 amino acids, or 1-6 amino acids, or 1-5 amino acids, or 1-4 amino acids, or 1-3 amino acids, or 1-2 amino acids or 1 amino acid from amino acids 1 to 750 of SEQ ID NOS: 2, 4, 6 and/or 8, wherein the term "differ" means that the given number of amino acids have been substituted, deleted and/or inserted when compared to the amino acid sequence of SEQ ID NOS: 2, 4, 6, 8.

A polypeptide of the present invention preferably comprises the amino acid sequence of SEQ ID NOS: 2, 4, 6 and/or 8 or variants thereof; or fragments thereof having isoamylase activity. The variants may in particular be an allelic variant, an artificial variant or a variant comprising a substitution, deletion, and/or insertion of one or more (several) amino acids of the mature polypeptide of SEQ ID NOS: 2, 4, 6 and/or 8. In a preferred aspect, the polypeptide comprises the amino acid sequence of SEQ ID NOS: 2, 4, 6 and/or 8. In another preferred aspect, the polypeptide comprises the mature polypeptide of SEQ ID NO: 2, 4, 6, and/or 8. In another preferred aspect, the polypeptide comprises amino acids 1 to 750 of SEQ ID NOS: 2, 4, 6 and/or 8 respectively, or a variant thereof; or fragments thereof having isoamylase activity. The variants may in particular be an allelic variant, an artificial variant or a variant comprising a substitution, deletion, and/or insertion of one or more (several) amino acids of the mature polypeptide of SEQ ID NOS: 2, 4, 6 and/or 8. In another preferred aspect, the polypeptide comprises amino acids 1 to 750 of SEQ ID NOS: 2, 4, 6 and/or 8. In another preferred aspect, the polypeptide consists of the amino acid sequence of SEQ ID NOS: 2, 4, 6 and/or 8; or variants thereof; or fragments thereof having isoamylase activity. The variants may in particular be an allelic variant, an artificial variant or a variant comprising a substitution, deletion, and/or insertion of one or more (several) amino acids of the mature polypeptide of SEQ ID NOS: 2, 4, 6 and/or 8. In another preferred aspect, the polypeptide consists of the amino acid sequence of SEQ ID NOS: 2, 4, 6 and/or 8. In another preferred aspect, the polypeptide consists of the mature polypeptide of SEQ ID NOS: 2, 4, 6 and/or 8. In another preferred aspect, the polypeptide consists of amino acids 1 to 750 of SEQ ID NOS: 2, 4, 6 and/or 8; or a variant thereof; or a fragment thereof having isoamylase activity. The variant may in particular be an allelic variant, an artificial variant or a variant comprising a substitution, deletion, and/or insertion of one or more (several) amino acids of the mature polypeptide of SEQ ID NOS: 2, 4, 6 and/or 8. In another preferred aspect, the polypeptide consists of amino acids 1 to 750 of SEQ ID NOS: 2, 4, 6 and/or 8.

In a second aspect, the present invention relates to an isolated polynucleotide encoding polypeptides having isoamylase activity, obtained by:

(a) hybridizing a population of DNA under at least high stringency conditions, preferably at least very high stringency conditions with (i) the mature polypeptide coding sequence of SEQ ID NO: 1, SEQ ID NO: 3, SEQ ID NO: 5 and/or SEQ ID NO: 7 (ii) the genomic DNA sequence comprising the mature polypeptide coding sequence of SEQ ID NO: 1, SEQ ID NO: 3, SEQ ID NO: 5 and/or SEQ ID NO: 7, or (iii) a full-length complementary strand of (i) or (ii);

(b) isolating the hybridized polynucleotide, which encodes a polypeptide having isoamylase activity.

Therefore, the invention relates to isolated polypeptides having isoamylase activity that are encoded by polynucleotides that hybridize under preferably high stringency conditions, preferably very high stringency conditions with (i) the mature polypeptide coding sequence of SEQ ID NO: 1, 3, 5, and/or 7, (ii) the genomic DNA sequence comprising the mature polypeptide coding sequence of SEQ ID NO: 1, 3, 5 and/or 7, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, New York). A subsequence of the mature polypeptide coding sequence of SEQ ID NOS: 1, 3, 5 and/or 7, respectively, contain at least 100 contiguous nucleotides or preferably at least 200 contiguous nucleotides. Moreover, the subsequence may encode a polypeptide fragment having isoamylase activity. In a preferred aspect, the complementary strand is the full-length complementary strand of the mature polypeptide coding sequence of SEQ ID NOS: 1, 3, 5 and/or 7.

The nucleotide sequence of SEQ ID NOS: 1, 3, 5 and/or 7; or a subsequence thereof; as well as the amino acid sequence of SEQ ID NOS: 2, 4, 6 and/or 8; or fragments thereof; may be used to design nucleic acid probes to identify and clone DNA encoding polypeptides having isoamylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length.

For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other strains may, therefore, be screened for DNA that hybridizes with the probes described above and encodes a polypeptide having isoamylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NOS: 1, 3, 5 and/or 7; or subsequences thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NOS: 1, 3, 5 and/or 7; the genomic DNA sequence comprising the mature polypeptide coding sequence of SEQ ID NOS: 1, 3, 5, and/or 7; its full-length complementary strands; or a subsequence thereof; under high to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NOS: 1, 3, 5 and/or 7. In another preferred aspect, the nucleic acid probe is nucleotides 79 to 2328 of SEQ ID NOS: 1, 3, 5 and/or 7, respectively. In another preferred aspect, the nucleic acid probe is a polynucleotide sequence that encodes the polypeptide of SEQ ID NOS: 2, 4, 6 and/or 8, or a subsequence thereof. In another preferred aspect, the nucleic acid probe is SEQ ID NOS: 1, 3, 5 and/or 7. In another preferred aspect, the nucleic acid probe is one of the polynucleotide sequences contained in and obtainable from deposited strains *Dyella japonica* DSM 22712, *Dyella japonica* DSM 22713, *Dyella japonica*

DSM 22714 and/or *Dyella japonica* DSM 22715, wherein the polynucleotide sequence thereof encodes polypeptides having isoamylase activity. In another preferred aspect, the nucleic acid probe is the mature polypeptide coding region contained in and obtainable from deposited strains *Dyella japonica* DSM 22712, *Dyella japonica* DSM 22713, *Dyella japonica* DSM 22714 and/or *Dyella japonica* DSM 22715.

For long probes of at least 100 nucleotides in length, high and very high stringency conditions are defined as prehybridization and hybridization at 42° C. in 5×SSPE, 0.3% SDS, 200 micro g/ml sheared and denatured salmon sperm DNA, and 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having isoamylase activity encoded by polynucleotides comprising or consisting of (c1) a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 1;

(c2) a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 3;

(c3) a nucleotide sequence having at least 86%, preferably at least 88%, more preferably at least 90%, more preferably at least 92%, even more preferably at least 95%, most preferably at least 97%, and even most preferably at least 99% identity to the mature polypeptide coding sequence of SEQ ID NO: 5;

(c4) a nucleotide sequence having at least 84%, preferably at least 86%, more preferably at least 87%, more preferably at least 88%, more preferably at least 89%, more preferably at least 90%, more preferably at least 92%, even more preferably at least 95%, most preferably at least 97%, and even most preferably at least 99% identity to the mature polypeptide coding sequence of SEQ ID NO: 7.

In a fourth aspect, the present invention relates to artificial variants comprising a substitution, deletion, and/or insertion of one or more (or several) amino acids of the mature polypeptide of SEQ ID NOS: 2, 4, 6 and/or 8; or homologous sequences thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

The amino acid substitutions in the wild-type polypeptide include both substitutions with the 20 standard amino acids but also non-standard amino acids (such as 4-hydroxyproline, 6-N-methyl lysine, 2-aminoisobutyric acid, isovaline, and alpha-methyl serine). A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., isoamylase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223, 409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NOS: 2, 4, 6 and/or 8, is 10, preferably 9, more preferably 8, more preferably 7, more preferably at most 6, more preferably 5, more preferably 4, even more preferably 3, most preferably 2, and even most preferably 1.

Sources of Polypeptides Having Isoamylase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly. Examples of sources from which a polypeptide of the present invention may be obtained include but are not limited to any of the following described below.

A polypeptide having isoamylase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having isoamylase activity, or a Gram negative bacterial polypeptide such as a *Dyella, Fulvimonas, Frateuria* and *Rhodanobacter E. coli, Pseudomonas, Salmonella, Campylobacter, Helicobacter, Flavobacterium, Fusobacterium, Ilyobacter, Neisseria,* or *Ureaplasma* polypeptide having isoamylase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having isoamylase activity.

In another preferred aspect, the polypeptide is a *Streptococcus equisimilis, Streptococcus pyogenes, Streptococcus uberis,* or *Streptococcus equi* subsp. *Zooepidemicus* polypeptide having isoamylase activity.

In another preferred aspect, the polypeptide is a *Streptomyces achromogenes, Streptomyces avermitilis, Streptomyces coelicolor, Streptomyces griseus,* or *Streptomyces lividans* polypeptide having isoamylase activity.

In another preferred aspect, the polypeptide is a *Pseudomonas amyloderamosa* polypeptide, e.g., the one described in (Harada et al., 1968; Sugimoto et al., 1974) having isoamylase activity.

In another preferred aspect, the polypeptide is a *Frateuria aurantia* polypeptide having isoamylase activity.

In another preferred aspect, the polypeptide is a *Dyella japonica* and *Dyella koreensis* polypeptide having isoamylase activity.

In a more preferred aspect, the polypeptide is a *Dyella japonica* polypeptide having isoamylase activity. In a most preferred aspect, the polypeptide is a *Dyella japonica* DSM 22712 DSM 22713, DSM 22714 and/or DSM 22715 polypeptide having isoamylase activity, e.g., the polypeptides comprising the mature polypeptides of SEQ ID NOS: 2, 4, 6 or 8, respectively.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having isoamylase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site (SEQ ID NO: 21), which is cleaved by a Factor Xa protease after the arginine residue (Eaton et al., 1986, *Biochem.* 25: 505-512); an Asp-Asp-Asp-Asp-Lys site (SEQ ID NO: 22), which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site (SEQ ID NO: 23), which is cleaved by thrombin after the Arg (Stevens, 2003, *Drug Discovery World* 4: 35-48); a Glu-Asn-Leu-Tyr-Phe-Gln-Gly site (SEQ ID NO: 24), which is cleaved by TEV protease after the Gln (Stevens, 2003, supra); and a Leu-Glu-Val-Leu-Phe-Gln-Gly-Pro site (SEQ ID NO: 25), which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having isoamylase activity of the present invention.

The polypeptide of the present invention may in particular be encoded by a polynucleotide comprising or consisting of any of the nucleotide sequences of SEQ ID NOS: 1, 3, 5 and/or 7; or a subsequence thereof encoding a fragment having isoamylase activity.

In a preferred aspect, the nucleotide sequence comprises or consists of SEQ ID NOS: 1, 3, 5 and/or 7, respectively. In another more preferred aspect, the nucleotide sequence comprises or consists of the sequence contained in the deposited strain: *Dyella japonica* NN060811 (DSM 22712); *Dyella japonica* NN060812 (DSM 22713); *Dyella japonica* NN060813 (DSM 22714); *Dyella japonica* NN060814 (DSM 22715).

In another preferred aspect, the nucleotide sequence comprises or consists of the mature polypeptide coding sequence of SEQ ID NOS: 1, 3, 5 and/or 7.

The present invention also encompasses nucleotide sequences that encode polypeptides comprising or consisting of the amino acid sequence of SEQ ID NOS: 2, 4, 6 and/or 8, respectively, or the mature polypeptide thereof, which differ from SEQ ID NOS: 1, 3, 5 and/or 7 or the mature polypeptide coding sequences thereof by virtue of the degeneracy of the genetic code. The present invention also relates to subsequences of SEQ ID NOS: 1, 3, 5 and/or 7 that encode fragments of SEQ ID NOS: 2, 4, 6 and/or 8, respectively, that have isoamylase activity.

The present invention also relates to mutant polynucleotides comprising or consisting of at least one mutation in the mature polypeptide coding sequence of SEQ ID NOS: 1, 3, 5 and/or 7, in which the mutant nucleotide sequence encodes the mature polypeptide of SEQ ID NOS: 2, 4, 6 and/or 8.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Dyella*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NOS: 1, 3, 5 and/or 7, respectively.

The present invention also relates to isolated polynucleotides encoding polypeptides having isoamylase activity, obtained by:

(a) hybridizing a population of DNA under at least high stringency conditions, preferably at least very high stringency conditions, with (i) the mature polypeptide coding sequence of SEQ ID NO: 1, SEQ ID NO: 3, SEQ ID NO: 5 and/or SEQ ID NO: 7 (ii) the genomic DNA sequence comprising the mature polypeptide coding sequence of SEQ ID NO: 1, SEQ ID NO: 3, SEQ ID NO: 5 and/or SEQ ID NO: 7, or (iii) a full-length complementary strand of (i) or (ii);

(b) isolating the hybridized polynucleotide, which encodes a polypeptide having isoamylase activity.

The isolated polynucleotide of the invention may be the mature polypeptide coding sequence in nucleotides 79-2328 of SEQ ID NOS: 1, 3, 5 and/or 7.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NOS: 1, 3, 5 and/or 7, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for isoamylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

In a preferred aspect, the complementary strand is the full-length complementary strand of the mature polypeptide coding sequence of SEQ ID NOS: 1, 3, 5 and/or 7.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

The present invention also relates to a nucleic acid construct comprising an isolated polynucleotide comprising a nucleotide sequence that encodes the polypeptide of the present invention, operably linked to one or more (several) control sequences that direct the production of the polypeptide in an expression host.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Combinations of promoters may also be used, such as the triple promoter system described in WO 99/43835 or example 1 of the present application, which consists of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Examples of terminators for bacterial host cells include but are not limited to those obtained from the genes of *Bacillus licheniformis* BPN' and *Bacillus licheniformis* amyl.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention. Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), *Bacillus clausii* alcaline protease (aprH) and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids −26 to −1 of SEQ ID NOS: 2, 4, 6 and/or 8, respectively. In another preferred aspect, the signal peptide coding sequence comprises or consists of nucleotides 1 to 78 of SEQ ID NOS: 1, 3, 6 and/or 8, respectively.

The control sequence may also be a propeptide coding sequence that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems.

In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also related to a recombinant expression vector comprising a nucleic acid construct of the present invention.

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5′-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The present invention also relates to a recombinant host cell comprising a nucleic acid construct of the present invention.

The host cell may be any cell useful in the recombinant production of a polypeptide of the present invention, e.g., a prokaryote or a eukaryote.

The prokaryotic host cell may be any gram-positive bacterium or a gram-negative bacterium. Gram-positive bacteria include, but are not limited to, *Bacillus, Streptococcus, Streptomyces, Staphylococcus, Enterococcus, Lactobacillus, Lactococcus, Clostridium, Geobacillus*, and *Oceanobacillus*. Gram-negative bacteria include, but are not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biol-* ogy 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus foetidus*, *Aspergillus fumigatus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Dyella*. In a more preferred aspect, the cell is *Dyella japonica*. In a most preferred aspect, the cell is *Dyella japonica* DSM 22712, *Dyella japonica* DSM 22713, *Dyella japonica* DSM 22714 and/or *Dyella japonica* DSM 22715, respectively.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to a method of producing the polypeptide of the present invention, comprising: (a) cultivating a host cell comprising a nucleic acid construct comprising a nucleotide sequence encoding the polypeptide under conditions conducive for production of the polypeptide; and (b) recovering the polypeptide. The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NOS: 1, 3, 5 and/or 7, wherein the mutant nucleotide sequence encodes a polypeptide that comprises or consists of the mature polypeptide of SEQ ID NOS: 2, 4, 6 and/or 8, respectively, and (b) recovering the polypeptide.

The present invention also relates to a method of producing a polypeptide of the present invention, comprising: (a) cultivating a transgenic plant or a plant cell comprising a polynucleotide encoding the polypeptide under conditions conducive for production of the polypeptide; and (b) recovering the polypeptide. In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

The polypeptides of the present invention may in a particular embodiment be purified by starch affinity chromatography, e.g., by using amylase-agarose as the affinity material. Methods of performing this include but are not limited to the method described below in example 2.

Plants

The present invention also relates to plants, e.g., a transgenic plant, plant part, or plant cell, comprising an isolated polynucleotide encoding a polypeptide having isoamylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The present invention also relates to a transgenic plant, plant part or plant cell transformed with a polynucleotide encoding a polypeptide of the present invention.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having isoamylase activity of the present invention under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the isoamylase activity of the composition has been increased, e.g., with an enrichment factor of at least 1.1.

The composition may comprise an isoamylase of the present invention as the major enzymatic component, e.g., a mono-component composition. In an embodiment the composition may further comprise one or more glucoamylases, in particular derived from a strain of the genus *Aspergillus, Trichoderma, Talaromyces* or *Trametes*, including *Aspergillus niger, Talaromyces emersonii, Trametes cingulata*, and *Trichoderma reesei*. In another embodiment the composition further comprising one or more additional enzymes selected from the group of proteases, alpha-amylases, beta-amylases, maltogenic amylases, alpha-glucosidases, pullulanases, hexosyltransferase and branching enzymes.

The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

The dosage of the polypeptide composition of the invention and other conditions under which the composition is used may be determined on the basis of methods known in the art.

Uses

The present invention is also directed to methods for using the polypeptides having isoamylase activity, or compositions thereof.

In one embodiment an isoamylase of the invention may be used in beverage, such as beer, mashing process.

In an embodiment an isoamylase of the invention may be used in the production of food ingredients from starch. Isoamylase are typically used in combination with other starch-hydrolysing enzymes, such as alpha-amylase, beta-amylase and glucoamylase. Depending on the specific application, isoamylase is used at levels between 50-5000 IAU per gram starch.

In the production of glucose syrup from starch, starch is liquefied using alpha-amylase, such as bacterial alpha-amylase, e.g., one or more *Bacillus* alpha-amylase. Subsequently, glucoamylase may be added to convert the starch hydrolysate to glucose syrup. The addition of isoamylase of the invention may then result in syrup with higher glucose content while reducing the amount of added glucoamylase.

Thus the present invention also relates to the use of an isoamylase of the present invention or a composition of the present invention for producing a glucose syrup.

The present invention also relates to the use of an isoamylase of the present invention or a composition of the present invention for a process for producing high fructose syrup process, in particular for producing HFCS.

Specific examples of the methods contemplated for high DX glucose syrup (e.g., 97-98 DX) production using mixtures of glucoamylase and isoamylase are described in U.S. Pat. No. 4,335,208, in particular examples 1, 3, 4, 5, 6 and 7, which is hereby incorporated by reference.

The present invention also relates to the use of an isoamylase of the present invention or a composition of the present invention in a process for producing maltose or maltitol.

An isoamylase of the invention may also be used in the production of maltose and maltitol.

In such embodiment the isoamylase is added to liquefied starch after being subjected to alpha-amylase. At the same time, beta-amylase may be added. The hydrolysis may be carried out at temperature around 50-60° C., e.g., at 50-55° C., and a pH of around pH 4-6, e.g., about 5.0). The resulting high maltose syrup may subsequently be purified and concentrated and subjected to crystallization to obtain crystalline maltose. Maltose may then be converted to maltitol by the catalytic hydrogenation. Maltitol is used as a sugar substitute in the production of non-cariogenic hard candies, chewing gum, and other confectionary.

An isoamylase of the invention may also be used together with cyclodextrin glucanotransferase (CGTase), malto-oligosyl trehalose synthase, and malto-oligosyl trehalose trehalohydrolase in the production of a disaccharide trehalose from liquefied starch. The reaction product is trehalose syrup, which is subsequently purified and concentrated. Trehalose is used in food (for example, in bakery goods, beverages, confectionery, and breakfast cereals) as a texturizer, stabilizer, humectant, and sweetener.

An isoamylase of the invention may also be used in conjunction with CGTase to enhance the production of cyclodextrins from starch. For example, a 90% yield of beta-cyclodextrin from amylopectin was obtained by applying a mixture of isoamylase, CGTase, and cyclodecanone at around pH 6 and 25° C. Cyclodecanone is a complexant that forms an insoluble inclusion complex with a cyclodextrin molecule. Cyclodextrins are used as encapsulating agents for food additives, flavours, and vitamins.

Generally isoamylase activity is preferably used in amounts of 1 to 1,000,000,000 IAU/kg DS, more preferably 10 to 100,000,000 IAU/kg DS, even more preferably 100 to 10,000,000 IAU/kg DS, and most preferably 50,000 to 5,000,000 IAU/kg DS or 0.001 mg to 100,000 mg EP/kg DS, preferably in the amount of 0.01 mg to 10,000 mg EP/kg DS, more preferably in the amount of 0.1 mg to 1,000 mg EP/kg DS, most preferably in the amount of 1 mg to 100 mg EP/kg DS.

The invention also relates to a method of producing glycogen using an isoamylase, branching enzyme and amylomaltase (EC 2.4.1.25), e.g., as described by Kajuura et al., 2008, *Biocatalysis and Biotransformation* 26(1-2): 133-140.

Materials & Methods

Materials

Alpha-Amylase LS: Blend of 2 parts hybrid alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+A181T+N190F+I201F+A209V+Q264S and 1 part *Bacillus stearothermophilus* alpha-amylase with the following mutations: I181*+G182*+N193F.

Glucoamylase AN: Glucoamylase from *Aspergillus niger*.

Glucoamylase T: Glucoamylase derived from *Talaromyces emersonii* disclosed in SEQ ID NO: 7 in WO 99/28448 and available from Novozymes NS, Denmark.

Deposit of Biological Material

The following biological material has been deposited under the terms of the Budapest Treaty with the Deutsche Sammlung von Mikroorganismen and Zellkulturen GmbH (DSMZ), Inffenstr. 7 B, D-38124 Braunschweig, Germany, and given the following accession number:

| Deposit | Accession Number | Date of Deposit |
| --- | --- | --- |
| *Dyella japonica* NN060811 | DSM 22712 | Jun. 24, 2009 |
| *Dyella japonica* NN060812 | DSM 22713 | Jun. 24, 2009 |
| *Dyella japonica* NN060813 | DSM 22714 | Jun. 24, 2009 |
| *Dyella japonica* NN060814 | DSM 22715 | Jun. 24, 2009 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Origin of Deposited Donor Strains

| Deposit | Country of Origin | Year |
| --- | --- | --- |
| *Dyella japonica* NN060811 | Denmark | 2007 |
| *Dyella japonica* NN060812 | China | 2007 |
| *Dyella japonica* NN060813 | China | 2007 |
| *Dyella japonica* NN060814 | China | 2007 |

Methods:
Determination of Isoamylase Activity Units (IAU)

The debranching of starch is measured as an increase in iodine binding and thereby increases in blue color due to the fact that linear glucans binds iodine more strongly than branched glucans (amylopectin).

1 unit (U) of isoamylase activity (IAU) is the amount of enzyme which causes an increase in absorbency of 0.01 per minute at 610 nm at 40° C., pH 4.5.

Substrate: 1% waxy corn starch (amylopectin) in 75 mM Na-acetate pH 4.5, 2 mM $CaCl_2$. The substrate should be boiled for 10-15 minutes to solubilise the starch.

Iodine/stop reagent: 10 mM $I_2$/KI in MQ $H_2O$

Sulphuric acid solution: 20 mM $H_2SO_4$ in MQ $H_2O$

Assay Procedure:

Mix
1. 600 microL substrate
2. 100 microL enzyme solution (include a control which should be 100 microL MQ $H_2O$)
3. Incubate at 40° C., 30 minutes
4. Withdraw 50 microL after 30 minutes into an eppendorf tube which already contains 50 microL of the iodine solution.
5. Subsequently add 1.5 mL of the sulphuric acid solution and transfer 200 microL to a MTP plate.
6. After 5 minutes read the absorbance at 610 nm Activity Calculation:

U/mL=OD610 (sample)−OD610 (control)/0.01/30 minutes/50 microL*1000 microL

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes NS, Denmark, which folder is hereby included by reference.

The present invention is further described by the following examples that should not be construed as limiting the scope of the invention.

EXAMPLES

Chemicals used as buffers and substrates were commercial products of at least reagent grade.

Example 1

Cloning and Expression of Four Isoamylases from *Dyella japonica* in *Bacillus subtilis*

A linear integration vector-system was used for the expression cloning of four isoamylase genes. The linear integration construct was a PCR fusion product made by fusion of each gene between two *Bacillus subtilis* homologous chromosomal regions along with a strong promoter and a chloramphenicol resistance marker. The fusion was made by SOE PCR (Horton, Hunt, Ho, Pullen, and Pease, 1989, Engineering hybrid genes without the use of restriction enzymes, gene splicing by overlap extension, *Gene* 77: 61-68). The SOE PCR method is also described in WO 2003/095658. Each gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as marker. (Described in, e.g., Diderichsen, Poulsen, and Joergensen, 1993, A useful cloning vector for *Bacillus subtilis*. *Plasmid* 30: 312). The final gene construct was integrated on the *Bacillus* chromosome by homologous recombination into the pectate lyase locus.

Chromosomal DNA of the four different *Dyella japonica* strains was isolated by QIAmp Tissue Kit (Qiagen, Hilden, Germany). For each gene construct three fragments were PCR amplified: the gene fragment from genomic DNA from the 4 *Dyella japonica* species (all primers used are listed in the Table 1 below), the upstream flanking fragment was amplified with the primers #01-iMB1362 and iMB1362Uni2 and the downstream flanking fragment was amplified with the primers #20-iMB1362 and oth435 from genomic DNA of the strain iMB1362 (described in WO 2003/095658).

The gene fragment was amplified using a proofreading polymerase (Phusion™ High-Fidelity DNA Polymerase, (New England Biolabs, Inc.)). The two flanking DNA fragments were amplified with "Expand High Fidelity PCR System" (Roche-Applied-Science). The PCR reactions were made according to standard procedures (following the manufacturer's recommendations). The PCR conditions were as follows: 94° C. for 2 minutes followed by 10 cycles of (94° C. for 15 seconds, 50° C. for 45 seconds, 68° C. for 4 minutes) followed by 20 cycles of (94° C. for 15 seconds, 50° C. for 45 seconds, 68° C. for 4 minutes (+20 seconds. extension per cycle)) and ending with one cycle at 68° C. for 10 minutes. The 3 resulting fragments were mixed in equal molar ratios and a new PCR reaction were run under the following conditions: initial 2 minutes at 94° C., followed by 10 cycles of (94° C. for 15 seconds, 50° C. for 45 seconds, 68° C. for 5 minutes), 10 cycles of (94° C. for 15 seconds, 50° C. for 45 seconds, 68° C. for 8 minutes), 15 cycles of (94° C. for 15 seconds, 50° C. for 45 seconds, 68° C. for 8 minutes in addition 20 seconds extra per cycle). After the $1^{st}$ cycle the two end primers #01-iMB1362: and #20-iMB1362 were added (20 pMol of each). Two microL of the PCR product was transformed into *Bacillus subtilis* and transformants was selected on LB-plates containing chloramphenicol (6 microg/mL medium). A clone containing the construct without mutations leading to amino acid changes was selected for fermentation in liquid media.

TABLE 1

Primers used

| Amplification of | SPECIFIC PRIMER FORWARD | SPECIFIC PRIMER REVERSE |
|---|---|---|
| *Dyella japonica* (NN060814) gen 1 | 5'-CTTGCTGCCTCATTCTGC AGCCGCGGCCATCAACAGCAT GACCTTG-3' (SEQ ID NO: 9) | 5'-GGGCCAAGGCCGGTTTTT TATGTTTTACTTCGAAATCAA CAACAACAGCG-3' (SEQ ID NO: 10) |
| *Dyella japonica* (NN060812) gen 2 | 5'-CTTGCTGCCTCATTCTGC CAGCGCGACACCGGCCCAGGC GGCCATCAAC-3' (SEQ ID NO: 11) | 5'-GGGCCAAGGCCGGTTTTT TATGTTTTACTTGGAAATCAG CAGCAGCAACGACTGGC-3' (SEQ ID NO: 12) |
| *Dyella japonica* (NN060813) gen 3 | 5'-CTTGCTGCCTCATTCTGC AGCCGCGGCCATCAACAGCAT GAGTCTTG-3' (SEQ ID NO. 13) | 5'-GGGCCAAGGCCGGTTTTT TATGTTTTACTTGGAGATCAG CAGCAACAGC-3' (SEQ ID NO: 14) |
| *Dyella japonica* (NN060811) gen 4 | 5'-CTTGCTGCCTCATTCTGC AGCCGCGGCCATCAACAGCAT GGGCCT-3' (SEQ ID NO: 15) | 5'-GGGCCAAGGCCGGTTTTT TATGTTTTACTTCGAGATCAG CAACAACAAAGACTG-3' (SEQ ID NO: 16) |
| upstream flanking fragment | #01-iMB1362: 5'-ACAATATGCGGGACG-3' (SEQ ID NO: 17) | iMB1362Uni2: 5'-CGCGGCTGCAGAATGAG GCA-3' (SEQ ID NO: 18) |
| downstream flanking fragment | oth435: 5'-TAAAACATAAAAAACCGG CCTTGGC-3' (SEQ ID NO: 19) | #20-iMB1362: 5'-GACATCAGCCCTGCT-3' (SEQ ID NO: 20) |

Fermentation

The clones was streaked on an LB-agar plates with 6 micro g/mL chloramphenicol from −80° C. stock, and grown overnight at 37° C. The colonies were transferred to 100 mL Cal-18 media in a 500 mL shaking flask. The culture was shaken at 26° C. at 170 rpm for 2 or 3 days. The cells were spun down and the enzyme purified from the supernatant by methods described in Example 2.

Example 2

Purification of *Dyella* isoamylase by Starch Affinity Chromatography

The crude ferment was filtered through a double filter paper sandwich layer consisting of the following grades of Whatman filter paper, D, A, B, C and F with F at the bottom. This crude filtration was then followed by vacuum filtration with a vacuum cup filter with a 0.2 micro m pore size cut off.

The volume of filtrate was recorded and $CaCl_2$ was added under slow stirring to give a final concentration of 1 mM. To 900 mL of filtrate add 100 mL of 1 M Sodium phosphate buffer pH 6.5 to give a final concentration of 0.1 M. It was checked that the pH was 6.5 and adjusted if necessary. The buffer addition may cause some precipitation, in this event the vacuum filtration step was repeated using a vacuum cup filter unit with a 0.2 micro m cut off.

Meanwhile a column was prepared (12×2.6 cm) with Amylose-agarose affinity column material (purchased from New England Biolabs) equilibrated with 0.1 M phosphate buffer pH 6.5. Load 200 mL of buffered culture filtrate mixture on to the column (5 mLs/min) and collect the flow through. The column was washed with 0.1 M phosphate buffer until the UV absorbance was stable (the wash was collected). The isoamylase was eluted from the column by washing the column with 0.1 M phosphate buffer+20% Maltose. The peak was collected when the absorbance started to climb over the base line level until the base line became stable again (ca. 50-100 mL total volume). The column was reconditioned with 0.1 M phosphate until a stable baseline was achieved and the load, wash, elute cycle was repeated until all the isoamylase supernatant was used up. After the first run a 4-20% Tris-glycine SDS page gel was run to check for the presence of the isoamylase in the load, column flow through, column wash and in the eluted fractions.

20 microL of sample was mixed with 20 microL of sample buffer and heated to 95° C. for 10 minutes. 20 microL was loaded to each lane and the gel was run at 35 mA for one hour. Protein bands were realized using simply Blue safe stain from Invitrogen. The *Dyella* isoamylase appeared as a single band at 80 kD.

Once purity had been achieved the isoamylase fractions were pooled and were then concentrated using Amicon Ultra ultracentrifuge units fitted with a 30 kD cut off membrane (spun at 3,000 rpm×g for 30 minutes, the filtrate was discarded and the load/concentrate cycle was continued until all the pooled fraction was used). Once concentrated, the concentrate was washed several times with 0.1 M phosphate buffer pH 6.5 to remove the 20% maltose. The concentrated isoamylase was removed with a pipette and saved. The inner membrane was washed several times with 0.1 M phosphate buffer and each wash was pooled with the concentrate (this is important as unspecific binding will result in significant sample loss). The final volume was recorded.

The absorbance was measured at 280 nm using the phosphate buffer to zero the spectrophotometer. If the absorbance was more than 2.0 the sample was diluted in 0.1 M phosphate buffer so that the absorbance reading failed within 0.5-1.5.

The protein concentration was calculated thus: A280 value/molar absorbance (calculated from the amino acid sequence)×dilution factor. The value obtained was in mg/ml.

The sample was formulated by adding glycerol to a final concentration of 50%.

Example 3

A spray-dried DE 11 maltodextrin, produced from common corn starch liquefied with Alpha-Amylase LS, was dissolved in deionized water and the pH and solids level adjusted to approximately 4.3 and 30% respectively. Aliquots of the substrate containing 15 g dry solids were transferred to 50 mL blue-cap flasks fitted with magnetic stirrers which were then placed in a water bath at 58° C. Different amounts of Glucoamylase AN and *Dyella japonica* isoamylase (NN060812) were then added according to the scheme below and the pH's adjusted to 4.3.

Samples were taken at set time intervals and the reaction stopped by heating the sample to boiling. After dilution and sterile filtration the samples were analyzed for D-glucose by HPLC.

| Glucoamylase AGU/g DS | *Dyella* isoamylase IAU/g DS | Reaction time (hours) | % D-glucose |
| --- | --- | --- | --- |
| 0.18 | 0 | 24 | 91.45 |
| 0.18 | 0 | 48 | 95.88 |
| 0.18 | 0 | 72 | 96.35 |
| 0.12 | 100 | 24 | 88.45 |
| 0.12 | 100 | 48 | 96.51 |
| 0.12 | 100 | 72 | 96.91 |

These data show that it is possible to obtain a higher D-glucose yield when combining *Dyella* isoamylase with *Aspergillus niger* glucoamylase. At the same time, the glucoamylase dosage can be significantly reduced.

Example 4

A DE 11 maltodextrin substrate was prepared as described in Example 2. Different amounts of Glucoamylase AN, Glucoamylase T and *Dyella japonica* isoamylase (NN060812) were added according to the scheme below. The saccharification reaction was carried out at 58° C., pH 4.3.

Samples were taken at set time intervals and the reaction stopped by heating the sample to boiling. After dilution and sterile filtration the samples were analyzed for D-glucose by HPLC.

| Glucoamylase AN AGU/g DS | Glucoamylase T AGU/g DS | *Dyella* isoamylase IAU/g DS | Reaction time (hours) | % D-glucose |
| --- | --- | --- | --- | --- |
| 0.18 | 0 | 0 | 24 | 91.45 |
| 0.18 | 0 | 0 | 48 | 95.88 |
| 0.18 | 0 | 0 | 72 | 96.35 |
| 0 | 0.24 | 0 | 24 | 82.49 |
| 0 | 0.24 | 0 | 48 | 89.98 |
| 0 | 0.24 | 0 | 72 | 92.72 |
| 0 | 0.24 | 100 | 24 | 89.27 |
| 0 | 0.24 | 100 | 48 | 94.67 |
| 0 | 0.24 | 100 | 72 | 95.59 |
| 0 | 0.24 | 200 | 24 | 92.20 |
| 0 | 0.24 | 200 | 48 | 96.16 |
| 0 | 0.24 | 200 | 72 | 96.46 |

These data show that it is possible to match the performance of Glucoamylase AN (*Aspergillus niger* glucoamylase) by using a dosage of 0.24 AGU/g DS Glucoamylase T (*Talaromyces emersonii* glucoamylase) and 100-200 IAU/g DS *Dyella japonica* isoamylase.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated polypeptide having isoamylase activity, which has at least 95% amino acid sequence identity to the amino acid sequence of amino acids 1-750 of SEQ ID NO: 4.

2. The polypeptide of claim 1, having at least 96% amino acid sequence identity to the amino acid sequence of amino acids 1-750 of SEQ ID NO: 4.

3. The polypeptide of claim 1, having at least 97% amino acid sequence identity to the amino acid sequence of amino acids 1-750 of SEQ ID NO: 4.

4. The polypeptide of claim 1, having at least 98% amino acid sequence identity to the amino acid sequence of amino acids 1-750 of SEQ ID NO: 4.

5. The polypeptide of claim 1, having at least 99% amino acid sequence identity to the amino acid sequence of amino acids 1-750 of SEQ ID NO: 4.

6. The polypeptide of claim 1, comprising or consisting of the amino acid sequence of SEQ ID NO: 4.

7. The polypeptide of claim 1, comprising or consisting of the amino acid sequence of amino acids 1-750 of SEQ ID NO: 4.

8. The polypeptide of claim 1, which is a fragment of the amino acid sequence of SEQ ID NO: 4 having isoamylase activity.

9. A composition comprising the isolated polypeptide of claim 1.

10. The composition of claim 9, further comprising a glucoamylase.

11. The composition of claim 10, wherein the glucoamylase is a *Talaromyces emersonii* glucoamylase.

12. The composition of claim 9, further comprising one or more enzymes selected from the group consisting of alpha-amylases, beta-amylases, maltogenic amylases, alpha-glucosidases, pullulanases, hexosyltransferases, proteases, and branching enzymes.

13. A method for producing a glucose syrup, comprising
    (a) liquefying starch with an alpha-amylase; and
    (b) treating the liquefied starch with a glucoamylase and the polypeptide of claim 1 to produce the glucose syrup.

14. A method for producing maltose, comprising
    (a) liquefying starch with an alpha-amylase;
    (b) treating the liquefied starch with a beta-amylase and the polypeptide of claim 1 to produce a maltose syrup; and
    (c) obtaining maltose from the maltose syrup.

15. A method for producing maltitol, comprising
    (a) liquefying starch with an alpha-amylase;
    (b) treating the liquefied starch with a beta-amylase and the polypeptide of claim 1 to produce a maltose syrup;
    (c) obtaining maltose from the maltose syrup; and
    (d) converting the maltose to maltitol.

* * * * *